United States Patent
Heimbecher et al.

(10) Patent No.: US 9,918,787 B2
(45) Date of Patent: Mar. 20, 2018

(54) MONITORING, MANAGING AND/OR PROTECTING SYSTEM AND METHOD FOR NON-TARGETED TISSUE

(75) Inventors: Reed R. Heimbecher, Hamel, MN (US); Saurav Paul, Minneapolis, MN (US); John M. Berns, Eagan, MN (US); Jeffrey A. Schweitzer, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 807 days.

(21) Appl. No.: 13/101,755

(22) Filed: May 5, 2011

(65) Prior Publication Data
US 2011/0276046 A1 Nov. 10, 2011

Related U.S. Application Data

(60) Provisional application No. 61/331,700, filed on May 5, 2010.

(51) Int. Cl.
*A61B 18/00* (2006.01)
*A61B 18/14* (2006.01)
(Continued)

(52) U.S. Cl.
CPC .......... *A61B 18/1492* (2013.01); *A61B 34/30* (2016.02); *A61B 90/04* (2016.02);
(Continued)

(58) Field of Classification Search
CPC ............ A61B 19/2203; A61B 18/1492; A61B 2018/00642; A61B 2018/0071;
(Continued)

(56) References Cited

U.S. PATENT DOCUMENTS 5,383,874 A * 1/1995 Jackson et al. .................... 606/1
5,584,830 A * 12/1996 Ladd .................. A61B 18/1206
606/31

(Continued)

FOREIGN PATENT DOCUMENTS

WO WO/2005/102199 11/2005
WO WO/2009/120982 10/2009

OTHER PUBLICATIONS

Bosnos M., Guillen-Rodriguez, J.M., He, D.S., Marcus, F.I., Early Assessment of Biophysical Parameters Predicts Lesion Formation During RF Energy Delivery In Vitro (2010). 33(9):1082-8. doi: 10.1111/j.1540-8159.2010.02799.x.*

*Primary Examiner* — Jaymi Della
*Assistant Examiner* — Eunhwa Kim
(74) *Attorney, Agent, or Firm* — Dykema Gossett PLLC

(57) ABSTRACT

A monitoring, managing and protecting system is provided that includes a monitoring probe working in conjunction with an ablating device. The probe is configured to be positioned in close proximity to a region of non-targeted tissue proximate an ablation site of targeted tissue and to be operatively connected to an electrical response assessment system or component. The probe includes an elongate shaft having proximal and distal ends, with a handle disposed at the proximal end thereof and a tissue monitoring and protecting apparatus disposed at the distal end thereof. The ablating device includes an elongate shaft having proximal and distal ends, with a handle mounted at the proximal end thereof and an ablation element mounted at the distal end thereof. The monitoring probe measures electrical characteristics of the non-targeted tissue and/or of the tissue between the monitoring electrode and the ablation electrode. The electrical response assessment system determines whether the tissue is being damaged based on the electrical measurements. The monitoring, managing and protecting
(Continued)

system can notify a practitioner based on the determination, or modify or stop the ablation procedure.

20 Claims, 37 Drawing Sheets

(51) Int. Cl.
*A61B 90/00* (2016.01)
*A61B 18/18* (2006.01)
*A61B 34/30* (2016.01)

(52) U.S. Cl.
CPC ........ *A61B 18/18* (2013.01); *A61B 2018/0022* (2013.01); *A61B 2018/00285* (2013.01); *A61B 2018/00642* (2013.01); *A61B 2018/00696* (2013.01); *A61B 2018/00714* (2013.01); *A61B 2018/00779* (2013.01); *A61B 2018/00869* (2013.01); *A61B 2018/00875* (2013.01); *A61B 2018/00898* (2013.01); *A61B 2018/00904* (2013.01); *A61B 2034/301* (2016.02)

(58) Field of Classification Search
CPC .. A61B 2018/00869; A61B 2018/0022; A61B 2018/00285; A61B 2018/00696; A61B 2018/00779; A61B 2018/00875
USPC .......................................................... 606/41
See application file for complete search history.

(56) References Cited

U.S. PATENT DOCUMENTS

| | | |
|---|---|---|
| 6,233,476 B1 | 5/2001 | Strommer |
| 6,423,057 B1* | 7/2002 | He .................... A61B 18/1206 606/34 |
| 6,635,054 B2 | 10/2003 | Fjield |
| 6,690,963 B2 | 2/2004 | Ben-Haim |
| 7,197,354 B2 | 3/2007 | Sobe |
| 7,263,397 B2 | 8/2007 | Hauck |
| 7,386,339 B2 | 6/2008 | Strommer |
| 7,536,218 B2 | 5/2009 | Govari |
| 7,848,789 B2 | 12/2010 | Govari |
| 2003/0139794 A1* | 7/2003 | Jenney et al. ................ 607/122 |
| 2004/0122420 A1* | 6/2004 | Amoah .............. A61B 18/1206 606/34 |
| 2004/0176757 A1 | 9/2004 | Sinelnikov |
| 2006/0052683 A1* | 3/2006 | Parker et al. .................. 600/372 |
| 2006/0106375 A1* | 5/2006 | Werneth et al. ................. 606/32 |
| 2007/0106287 A1* | 5/2007 | O'Sullivan ..................... 606/41 |
| 2007/0185486 A1* | 8/2007 | Hauck et al. ................... 606/41 |
| 2007/0225701 A1* | 9/2007 | O'Sullivan ..................... 606/41 |
| 2008/0077126 A1* | 3/2008 | Rashidi .......................... 606/34 |
| 2008/0243112 A1* | 10/2008 | De Neve ........................ 606/28 |
| 2008/0255642 A1* | 10/2008 | Zarins ............... A61B 18/1206 607/99 |
| 2009/0247942 A1 | 10/2009 | Kirschenman |
| 2009/0247943 A1 | 10/2009 | Kirschenman |
| 2009/0247944 A1 | 10/2009 | Kirschenman |
| 2009/0247993 A1 | 10/2009 | Kirschenman |
| 2009/0248042 A1 | 10/2009 | Kirschenman |
| 2010/0256558 A1 | 10/2010 | Olson |
| 2011/0015569 A1 | 1/2011 | Kirschenman |
| 2011/0118727 A1 | 5/2011 | Fish |

* cited by examiner

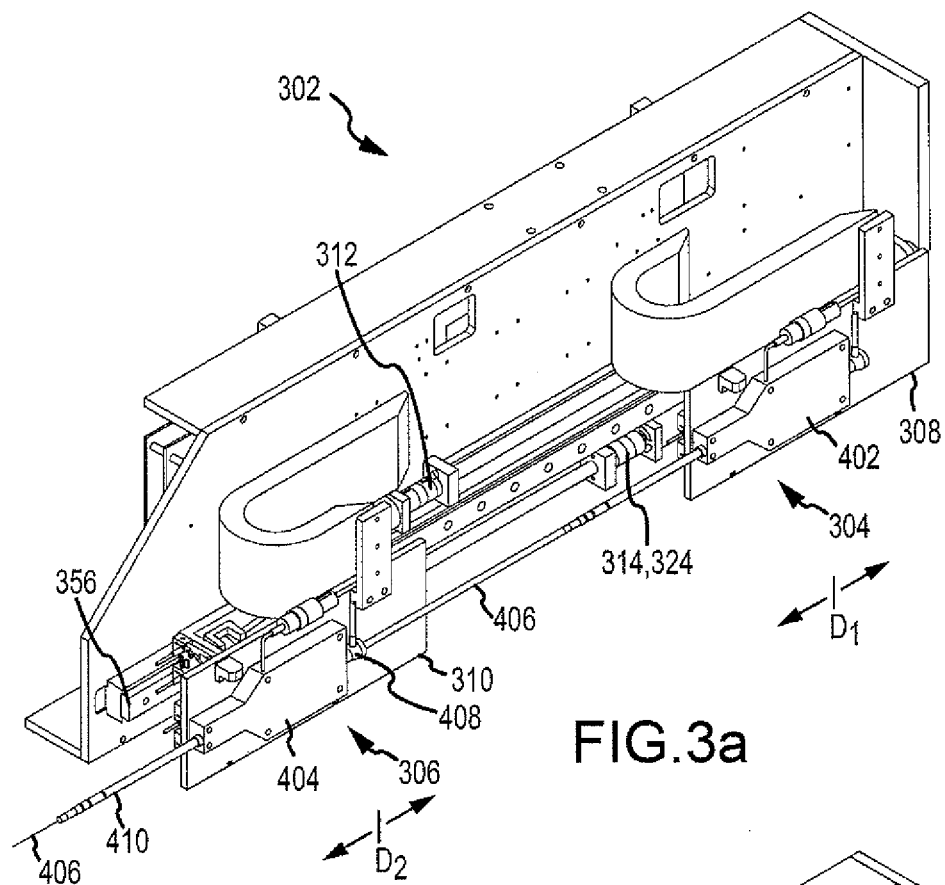
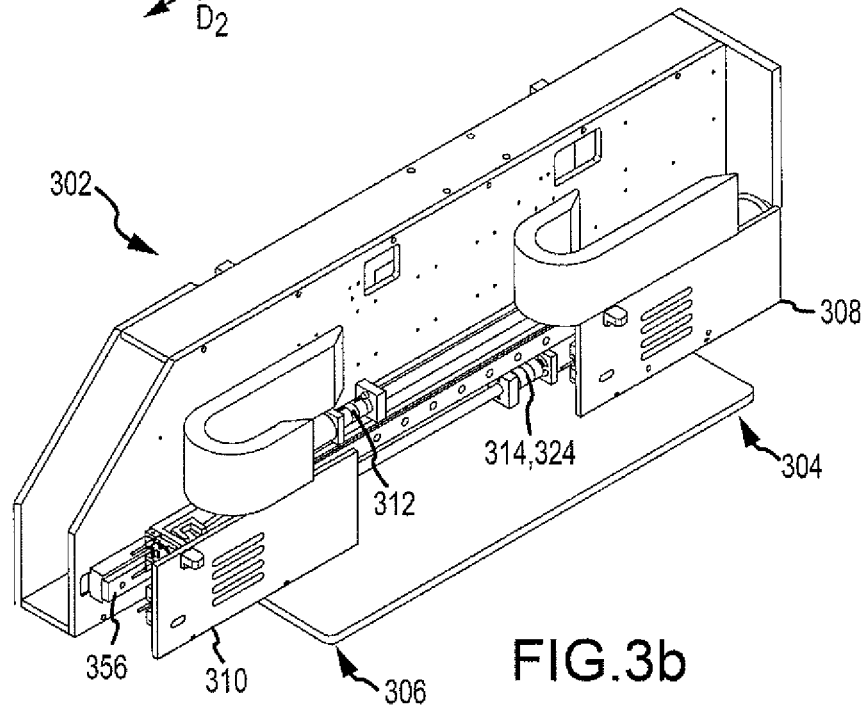

MONITORING, MANAGING AND/OR PROTECTING SYSTEM AND METHOD FOR NON-TARGETED TISSUE

CROSS-REFERENCE TO RELATED APPLICATIONS

This application claims the priority of U.S. provisional application No. 61/331,700, filed May 5, 2010, which is incorporated herein by reference as though fully set forth herein.

BACKGROUND OF THE INVENTION a. Field of the Invention

The present disclosure relates generally to medical systems for monitoring and protecting non-targeted tissue during the performance of medical procedures or therapeutic functions, such as, for example, ablation procedures. More particularly, the present disclosure relates to an esophageal monitoring, managing and protecting system for protecting non-targeted esophageal tissue during proximate ablation procedures, such as ablation procedures in the atrium.

b. Background Art

It is known to use minimally invasive surgical devices or ablating tools to perform ablation procedures in, for example, the heart. For instance, in treating a condition known as atrial fibrillation, it is known to advance an ablating tool through the vasculature of a patient to a desired location, and to then thermally ablate tissue within, for example, an ostium connecting a pulmonary vein to the heart, or to ablate the tissue within the heart surrounding the ostium.

Examples of the types of tools known in the art to perform such procedures are catheter-based ablating devices such as those described in U.S. Pat. No. 6,635,054 entitled "Thermal Treatment Methods and Apparatus with Focused Energy Application," U.S. Patent Publication No. 2004/0176757 entitled "Cardiac Ablation Devices," and International Publication No. WO 2005/102199 entitled "Ablation Devices with Sensor Structures." These devices generally include, among other components, an elongate shaft having a proximal end, a distal end, and a longitudinal axis extending therebetween. The devices further include an ablation element mounted at or near the distal end of the elongate shaft. In at least one such device, the ablation device is configured to emit ultrasonic waves with the strength and intensity to burn or ablate targeted tissue. Other ablation devices perform similar functions through the emission of RF energy.

In operation, once an ablating device is positioned in a desired location within the patient's anatomy (e.g., in the atrium), the ablation device is selectively activated to emit ablating energy (e.g., intense ultrasonic or RF energy). The energy is then directed forward and focused to define, for example, a region in the circumferential interior OS annular wall. Such a circumferential ablating device provides an efficient and effective means by which to simultaneously circumferentially ablate myocardial tissue around the OS of the pulmonary vein. Typically, multiple pulmonary ostia are ablated separately and sequentially with the same device as it is moved and placed in each OS needing ablation.

However, these known devices are not without their drawbacks. For instance, a drawback in known endocardial catheter pulmonary vein ostia ablation systems relates to the monitoring, maintenance, and/or control of the temperature in non-targeted tissue proximate the targeted ablation site during the ablation procedure. Such non-targeted tissue must not be damaged during the ablation procedure. More particularly, when certain heart tissue is being ablated, the energy emitted from the ablating device may be strong enough or generate a high enough temperature to cause tissue necrosis in non-targeted tissue.

As an example, since the esophagus which is generally located posterior to the atrium, RF ablation on the posterior atrial wall has been known to cause serious complications such as esophageal fistula. Such complications have even led to death of patients following RF ablation for treatment of Atrial Fibrillation (AF). Such complications are created by thermally-mediated damage to the esophagus due to overheating of the esophagus from uncontrollable application of RF energy during ablation on the posterior atrial wall.

Thermal monitoring of the esophagus to monitor and prevent such overheating has been proposed and tried, for example, the ProRhythm Esophageal Balloon. Such thermal monitoring techniques provide means of monitoring the temperature of the esophageal luminal wall. However, thermal monitoring of the luminal wall of the esophagus is generally inadequate in preventing such esophageal complications caused by ablation of the atrial wall.

At the outset, the temperature measurement of the esophageal wall is generally unreliable due the difficulty in accurately positioning the thermal probe in the esophagus relative to the ablation site on the atrial wall.

Even if the thermal probes are properly positioned in the esophagus, the threshold cut-off temperature to prevent esophageal complications cannot be set a priori. This is due to several factors, including that the thickness of the different tissue layers, such as for example, the pericardium, the fat layer, and the connective tissue, between the ablation electrode on the endocardial surface and the thermal sensors on the luminal wall of the esophagus, is not readily known. Further, the electric field and thermal properties of these tissue layers are not readily known. Based on these unknown variables, the thermal gradient from the endocardial site to the esophageal wall often cannot be readily determined. Consequently, the maximum temperature that can be allowed on the endocardial wall without creating dangerously high temperatures on the esophagus cannot be readily determined. The difficulty of reliably determining such temperatures on the endocardial side is further compounded by the unreliability of determining the endocardial tissue temperature during ablation.

If the thermal probes could reliably measure temperature of the esophageal luminal wall, that thermal information arrives after the fact that the esophageal wall has already attained potentially harmful temperature. This is due to the diffusive nature of the thermal field which has a long time constant. Thus, by the time the thermal probe senses a temperature rise in the luminal wall of the esophagus, it is usually too late for any preventative or corrective action.

Because of the aforementioned limitations, thermal monitoring of the esophageal luminal wall fails to provide a priori information that can be reliably used to adequately protect and prevent thermally-mediated esophageal injury during endocardial RF ablation of the posterior atrial wall during atrial fibrillation treatment. Accordingly, there is a need for an ablation tool, component and/or a system that will monitor, manage and/or protect non-targeted tissue during a medical procedure that functions to minimize or eliminate one or more of the above-identified deficiencies.

The present disclosure overcomes the above-described and other limitations of current monitoring and protecting of non-targeted tissue, such as the esophageal luminal wall, by electrically monitoring the targeted and/or non-targeted tissue conditions between the ablation electrode and the monitoring electrode, such as the tissue of and between the endocardial wall and the luminal wall of the esophagus, before and during ablation, and taking protective measures when necessary.

BRIEF SUMMARY OF THE INVENTION

The present disclosure is directed to a monitoring, managing and/or protecting system or component for use with various medical procedures, such as ablation procedures, to monitor and protect non-targeted tissue proximate to the location of the ablation procedure. An exemplary embodiment includes a system comprising a monitoring probe for determining electrical characteristics of the tissue in the esophagus proximate an ablation procedure in the atrium. The system and its constituent components monitor, manage and protect the non-targeted tissue including notifying the practitioner performing the ablation procedure when the non-targeted tissue may be damaged and/or controlling or stopping the ablation procedure when necessary to protect the non-targeted tissue.

In accordance with the present disclosure, an ablating device is configured to be inserted into the anatomy of a patient, such as in the atrium or heart chamber. This ablation device is capable of delivering ablating energy to a targeted tissue ablation site. The monitoring, managing and protective system of the present disclosure includes a monitoring and/or protective probe. The protective probe is also configured for insertion into the anatomy of a patient to be positioned in close proximity to a region of non-targeted tissue, which is proximate the ablation site. An example of such a non-targeted site may be the opposite side of the region of the targeted tissue from the ablating device or collateral to the targeted ablation site, such as the esophageal region opposite the atrium.

In one exemplary embodiment, the ablating device comprises an elongate shaft having a proximal end and a distal end. The ablating device further includes an ablation element mounted to the elongate shaft at the distal end. The ablation element may include an RF electrode for providing the energy necessary for the ablation procedure. In use, the elongate shaft and ablation device may be connected to a handle for manual control purposes. Alternatively, and as described in detail herein, the elongate shaft and electrode may be connected or coupled to a system for automatic assistance in medical procedures, such as a Robotic Catheter Guidance System (RCGS) for assisting and/or controlling an ablation catheter during an ablation procedure. The present disclosure, including the monitoring, managing and/or protecting system and catheter can be utilized with both automated and manual medical procedures.

In one exemplary embodiment, the monitoring and protecting probe includes a tubular body having a catheter shaft. The catheter shaft has a proximal portion, a distal portion, an anterior surface and posterior surface. The probe also has an anchoring device located at the distal portion of the catheter shaft. The anchoring device has an anterior surface and a posterior surface. The probe also contains a monitoring electrode, such as an esophageal electrode, which is operatively connected to an electrical response assessment system for measuring the electrical characteristics of tissue at the anterior luminal wall of the esophagus and/or between the anterior luminal wall of the esophagus and the posterior endocardial wall of the atrium. The esophageal monitoring, managing and protecting apparatus and system is configured to protect non-targeted tissue in the region of non-targeted tissue from receiving unintended ablation energy intentionally targeted at proximate opposed, collateral, or upbeam targeted tissue, such as, for example, ablation energy delivered to tissue opposite the region of non-targeted tissue from the tissue protecting apparatus.

In accordance with another aspect of the present disclosure, an apparatus for use in monitoring the electrical field, or tissue temperature or the position of an ablation electrode in a region of non-targeted tissue during an ablation procedure performed on targeted tissue proximate the region of non-targeted tissue is provided. The apparatus includes a probe configured to be inserted into the anatomy of a patient, such as the esophagus, and includes a proximal end and distal end. The apparatus further comprises an electrical field monitoring, temperature monitoring and/or position monitoring apparatus associated with the probe.

In accordance with another aspect of the present disclosure, a method of monitoring, managing and protecting a region of non-targeted tissue during an ablation procedure performed on targeted tissue proximate the region of non-targeted tissue is provided. The method comprises a first step of inserting an esophageal catheter in the esophagus such that an electrode on the esophageal catheter is aligned with and facing the posterior wall of the atrium. Next, an anchoring means is deployed such that the anterior surface of the anchoring means is facing the posterior wall of the atrium. After inserting an ablation electrode into the endocardial chamber, an electrical response assessment system or component is operatively connecting to the electrode on the esophageal catheter and may be operatively connected to the electrode in the endocardial chamber. The electrical response assessment system may be separate from, replace, or be incorporated into an electronic control system (ECS), which may include an electronic control unit (ECU) for assistance in controlling an RCGS and the ablation catheter. Once connected, the electrical characteristics of the tissue of the esophagus or the tissue between the esophageal and ablation electrodes can be measured and managed, including, during ablation of the posterior atrial wall, the electrical characteristics measured by the electrical response assessment system or component may be used to control or prevent ablation energy being delivered to the endocardial electrode. The monitoring, managing and/or protecting system or component can be used in conjunction with the RCGS, or separate from the RCGS and independent of the ablation catheter.

The foregoing and other aspects, features, details, utilities, and advantages of the present teachings will be apparent from reading the following description and claims, and from reviewing the accompanying drawings.

BRIEF DESCRIPTION OF THE DRAWINGS

FIGS. 3a-3b are isometric views of a manipulator assembly shown in FIG. 2, showing the ablation catheter and sheath manipulation mechanism in greater detail.

FIG. 9A is transverse plane view 9AA of FIG. 9.

FIG. 10A is transverse plane view 10AA of FIG. 10.

FIG. 11A is transverse plane view 11AA of FIG. 11.

FIG. 12A is transverse plane view 12AA of FIG. 12.

FIG. 13A is transverse plane view 13AA of FIG. 13.

FIG. 14A is transverse plane view 14AA of FIG. 14.

FIG. 15A is transverse plane view 15AA of FIG. 15.

FIG. 16A is transverse plane view 16AA of FIG. 16

FIG. 17A is transverse plane view 17AA of FIG. 17.

FIG. 18A is transverse plane view 18AA of FIG. 18.

FIG. 19A is transverse plane view 19AA of FIG. 19.

FIG. 20A is transverse plane view 20AA of FIG. 20.

FIG. 21A is transverse plane view 21AA of FIG. 21.

FIG. 22A is transverse plane view 22AA of FIG. 22.

FIG. 23A is transverse plane view 23AA of FIG. 23.

FIG. 24A is transverse plane view 24AA of FIG. 24.

FIG. 25A is transverse plane view 25AA of FIG. 25.

FIG. 26A is transverse plane view 26AA of FIG. 26.

FIG. 27A is transverse plane view 27AA of FIG. 27.

FIG. 28A is transverse plane view 28AA of FIG. 28.

FIG. 29A is transverse plane view 29AA of FIG. 29.

FIG. 30A is transverse plane view 30AA of FIG. 30.

FIG. 31A is transverse plane view 3 IAA of FIG. 31.

FIG. 32A is transverse plane view 32AA of FIG. 32.

FIG. 33A is transverse plane view 33AA of FIG. 33.

FIG. 34A is transverse plane view 34AA of FIG. 34.

FIG. 35A is transverse plane view 35AA of FIG. 35.

DETAILED DESCRIPTION OF THE INVENTION

The present disclosure is directed to a monitoring, managing and/or protecting system or component for use with various medical procedures, such as ablation procedures, to monitor and protect non-targeted tissue proximate to the location of the ablation procedure. The present invention is of aid in a number of procedure types, whether doctor controlled or automatically controlled, e.g., by a robotic system or magnetic system. The inventions monitor, manage and protect the non-targeted tissue including notifying the practitioner or the system performing the ablation procedure when the non-targeted tissue may be damaged and/or controlling or stopping the ablation procedure when necessary to protect the non-targeted tissue.

Before proceeding to a detailed description of the non-targeted tissue monitoring, managing and protecting system, a brief overview (for context) of one possible robotic control and guidance system (RCGS) for manipulating a medical device, such an ablation catheter, will first be described. The description of the RCGS will detail how several electric motors can be used to control the translation, distal bending and virtual rotation of a catheter and surrounding sheath. After the description of the RCGS, the present specification will then provide a description of the non-targeted tissue monitoring, managing and protecting system, and how the system can be used in conjunction with the RCGS in certain embodiments to control or assist in the control of the ablation catheter to monitor and protect a non-targeted tissue, such as the esophagus, during a medical procedure. Likewise, one of ordinary skill in the art will recognize that these inventions may also provide non-targeted tissue monitoring and procedure control in conjunction with any other automatic system and may also provide monitoring and control for a doctor manipulated catheter or procedure.

Figure 1:
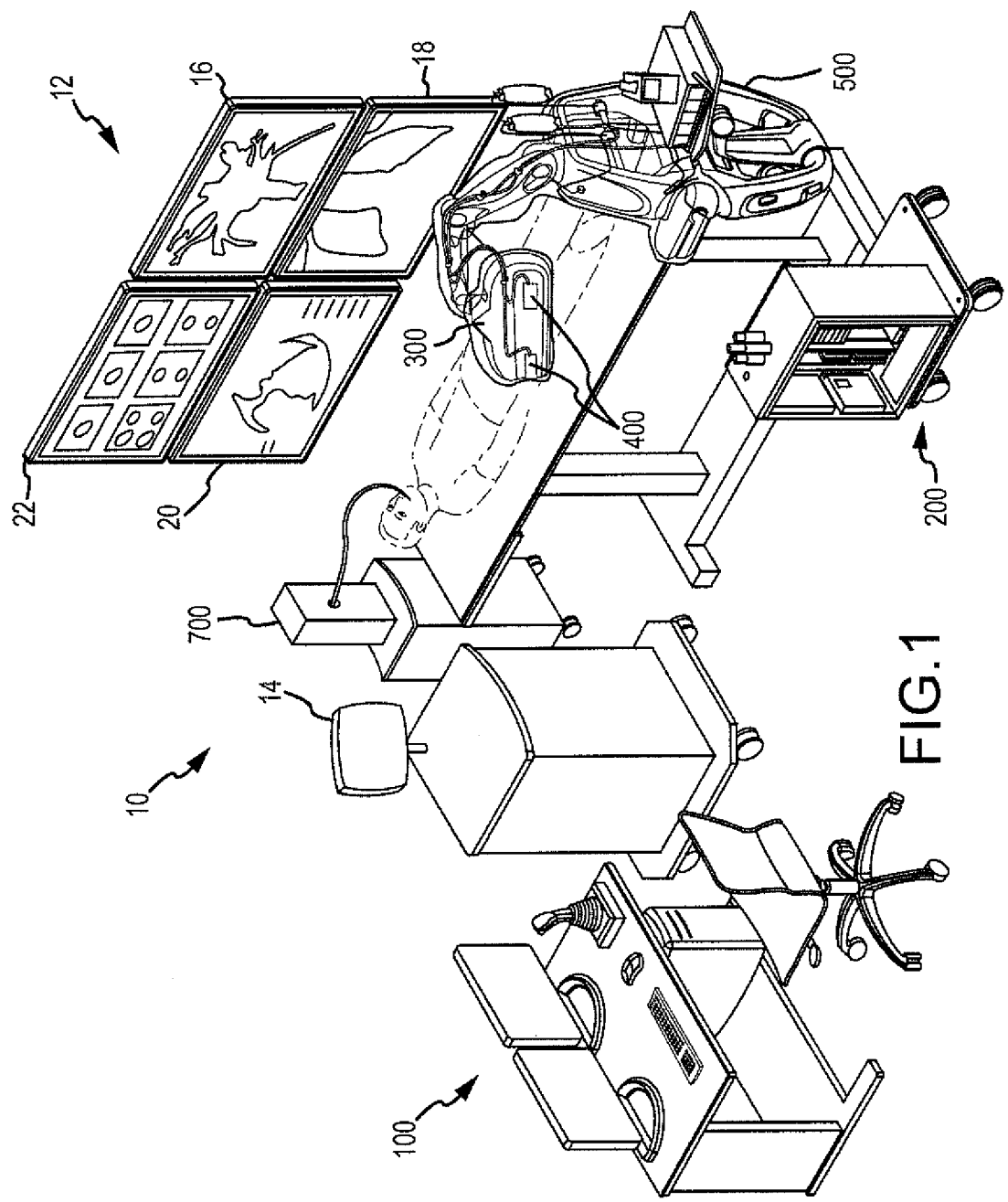
FIG. 1 is an isometric diagrammatic view of a Robotic Catheter Guidance System and a non-targeted tissue monitoring and protecting system, illustrating an exemplary layout of various system components.

Now referring to the drawings wherein like reference numerals are used to identify identical components in the various views, FIG. 1 is a diagrammatic view of an exemplary RCGS 10, in which several aspects of a system and method for automatic detection and prevention of motor runaway can be used. In addition to the description set forth herein, further details of an RCGS system can be found in commonly owned U.S. patent application Ser. No. 12/970,500 entitled "PROXIMITY SENSOR INTERFACE IN A ROBOTIC CATHETER SYSTEM", the entire disclosure of the application being hereby incorporated by reference.

Exemplary RCGS System Description. RCGS 10 can be likened to power steering for a catheter system, The RCGS 10 can be used, for example, to manipulate the location and orientation of catheters and sheaths in a heart chamber or in another body cavity or lumen. The RCGS 10 thus provides the user with a similar type of control provided by a conventional manually-operated system, but allows for repeatable, precise, and dynamic movements. For example, a user such as an electrophysiologist can identify locations (potentially forming a path) on a rendered computer model of the cardiac anatomy. The system can be configured to relate those digitally selected points to positions within a patient's actual/physical anatomy, and can thereafter command and control the movement of the catheter to the defined positions. Once at the specified target position, either the user or the system can perform the desired diagnostic or therapeutic function. The RCGS 10 enables full robotic navigation/guidance and control.

As shown in FIG. 1, the RCGS 10 can generally include one or more monitors or displays 12, a visualization, mapping and navigation (including localization) system 14, a human input device and control system (referred to as "input control system") 100, an electronic control system 200, a manipulator assembly 300 for operating a device cartridge 400, an actuation unit 600 (shown in FIG. 6), a manipulator support structure 500 for positioning the manipulator assembly 300 in proximity to a patient or a patient's bed, and a monitoring, managing and protecting system 700, for monitoring and protecting non-targeted tissue during a medical procedure.

Displays 12 are configured to visually present to a user information regarding patient anatomy, medical device location or the like, originating from a variety of different sources. Displays 12 can include (1) an ENSITE VELOCITY™ monitor 16 (coupled to system 14—described more fully below) for displaying cardiac chamber geometries or models, displaying activation timing and voltage data to identify arrhythmias, and for facilitating guidance of catheter movement; (2) a fluoroscopy monitor 18 for displaying a real-time x-ray image or for assisting a physician with catheter movement; (3) an intra-cardiac echo (ICE) display 20 to provide further imaging; and (4) an EP recording system display 22.

The system 14 is configured to provide many advanced features, such as visualization, mapping, navigation support and positioning (i.e., determine a position and orientation (P&O) of a sensor-equipped medical device, for example, a P&O of a distal tip portion of a catheter). Such functionality can be provided as part of a larger visualization, mapping and navigation system, for example, an ENSITE VELOCITY™ system running a version of NAVX™ software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present disclosure, and hereby incorporated by reference in its entirety. System 14 can comprise conventional apparatus known generally in the art, for example, the ENSITE VELOCITY™ system described above or other known technologies for locating/navigating a catheter in space (and for visualization), including for example, the CARTO visualization and location system of Biosense Webster, Inc., (e.g., as exemplified by U.S. Pat. No. 6,690,963 entitled "System for Determining the Location and Orientation of an Invasive Medical Instrument" hereby incorporated by reference in its entirety), the AURORA® system of Northern Digital Inc., a magnetic field based localization system such as the GMPS® system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3 visualization and location system of Biosense Webster, Inc. (e.g., as exemplified by U.S. Pat. Nos. 7,536, 218, and 7,848,789 both of which are hereby incorporated by reference in its entirety). Some of the localization, navigation and/or visualization systems can involve providing a sensor for producing signals indicative of catheter location and/or orientation information, and can include, for example one or more electrodes in the case of an impedance-based localization system such as the ENSITE VELOCITY™ system running NAVX™ software, which electrodes can already exist in some instances, or alternatively, one or more coils (i.e., wire windings) configured to detect one or more characteristics of a low-strength magnetic field, for example, in the case of a magnetic-field based localization system such as the GMPS® system using technology from MediGuide Ltd. described above.

The input control system 100 is configured to allow a User, such as an electrophysiologist, to interact with the RCGS 10, in order to control the movement and advancement/withdrawal of both a catheter and sheath (see, e.g., commonly assigned U.S. patent application Ser. No. 12/751,843 filed Mar. 31, 2010 entitled "ROBOTIC CATHETER SYSTEM" and PCT/US2009/038597 entitled "ROBOTIC CATHETER SYSTEM WITH DYNAMIC RESPONSE", published as WO 2009/120982; the entire disclosure of both applications being hereby incorporated by reference). Generally, several types of input devices and related controls can, be employed, including, without limitation, instrumented traditional catheter handle controls, oversized catheter models, instrumented user-wearable gloves, touch screen display monitors, 2-D input devices, 3-D input devices, spatially detected styluses, and traditional joysticks. For a further description of exemplary input apparatus and related controls, see, for example, commonly assigned U.S. patent application Ser. No. 12/933,063 entitled "ROBOTIC CATHETER SYSTEM INPUT DEVICE" and U.S. patent application Ser. No. 12/347,442 entitled "MODEL CATHETER INPUT DEVICE", the entire disclosure of both applications being hereby incorporated by reference. The input devices can be configured to directly control the movement of the catheter and sheath, or can be configured, for example, to manipulate a target or cursor on an associated display.

The electronic control system 200 is configured to translate (i.e., interpret) inputs (e.g., motions) of the user at an input device or from another source into a resulting movement of the catheter and/or surrounding sheath. In this regard, the system 200 includes a programmed electronic control unit (ECU) in communication with a memory or other computer readable media (memory) suitable for information storage. Relevant to the present disclosure, the electronic control system 200 is configured, among other things, to issue commands (i.e., actuation control signals) to the manipulator assembly 300 (i.e., to the actuation units—electric motors) to move or bend the catheter and/or sheath to prescribed positions and/or in prescribed ways, all in accordance with the received user input and a predetermined operating strategy programmed into the system 200. In addition to the instant description, further details of a programmed electronic control system can be found in commonly assigned U.S. patent application Ser. No. 12/751,843 filed Mar. 31, 2010 entitled "ROBOTIC CATHETER SYSTEM", described above. It should be understood that although the exemplary ENSITE VELOCITY™ System 14 and the electronic control system 200 are shown separately, integration of one or more computing functions can result in a system including an ECU on which can be run both (i) various control and diagnostic logic pertaining to the RCGS 10 and (ii) the visualization, mapping and navigation functionality of system 14.

The manipulator assembly 300, in response to such commands, is configured to maneuver the medical device (e.g., translation movement, such as advancement and withdrawal of the catheter and/or sheath), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations, as detailed below) for linearly actuating one or more control members (e.g., steering wires) associated with the medical device for achieving the above-described translation, deflection and/or rotation (or virtual rotation). In addition to the description set forth herein, further details of a manipulator assembly can be found in commonly assigned U.S. patent application Ser. No. 12/347,826 titled "ROBOTIC CATHETER MANIPULATOR ASSEMBLY", the entire disclosure of which is hereby incorporated by reference.

A device cartridge 400 is provided for each medical device controlled by the RCGS 10. For this exemplary description of an RCGS, one cartridge is associated with a catheter and a second cartridge is associated with an outer sheath. The cartridge is then coupled, generally speaking, to the RCGS 10 for subsequent robotically-controlled movement. In addition to the description set forth herein, further details of a device cartridge can be found in commonly owned U.S. patent application Ser. No. 12/347,835 entitled "ROBOTIC CATHETER DEVICE CARTRIDGE" and U.S. patent application Ser. No. 12/347,842 "ROBOTIC CATHETER ROTATABLE DEVICE CARTRIDGE", the entire disclosure of both applications being hereby incorporated by reference.

The monitoring, managing and protecting system 700 allows for the monitoring, managing and protecting of non-targeted tissue, such as the esophagus, during a medical procedure, such as an ablation. The monitoring, managing and protecting system 700 can communicate with the electronic control system 200 to transmit commands to the actuation unit 600 to modify or stop the medical procedure from continuing, thereby protecting the non-targeted tissue from damage or additional damage. Further, the monitoring, managing and protecting system 700 can also be configured to work independently from the electronic control system 200 and/or the RCGS 10, as described in detail below.

Figure 2:
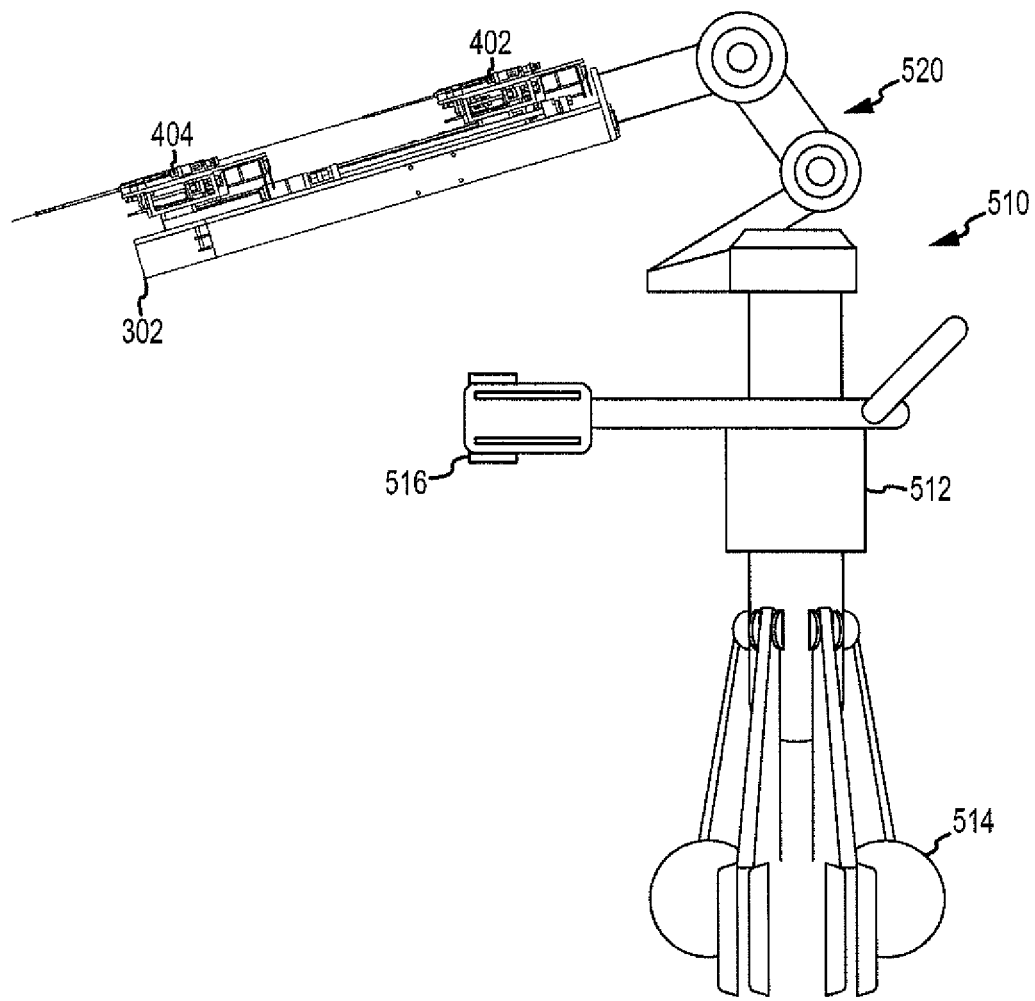
FIG. 2 is a side view of a manipulator assembly shown in FIG. 1, coupled to a robotic support structure, showing side views of ablation catheter and sheath manipulation mechanisms.

FIG. 2 is a side view of an exemplary robotic catheter manipulator support structure, designated structure 510 (see commonly owned U.S. patent application Ser. No. 12/347,811 entitled "ROBOTIC CATHETER SYSTEM" described above). The structure 510 can generally include a support frame 512 including retractable wheels 514 and attachment assembly 516 for attachment to an operating bed (not shown). A plurality of support linkages 520 can be provided for accurately positioning one or more manipulator assemblies, such as manipulator assembly 302. The assembly 302 is configured to serve as the interface for the mechanical control of the movements or actions of one or more device cartridges, such as catheter and sheath cartridges 402, 404 described below. Each device cartridge is configured to receive and retain a respective proximal end of an associated medical device (e.g., catheter or sheath). The assembly 302 also includes a plurality of manipulation bases onto which the device cartridges are mounted. After mounting, the manipulator assembly 302, through the manipulation bases, is capable of manipulating the attached catheter and sheath.

Figure 4A:
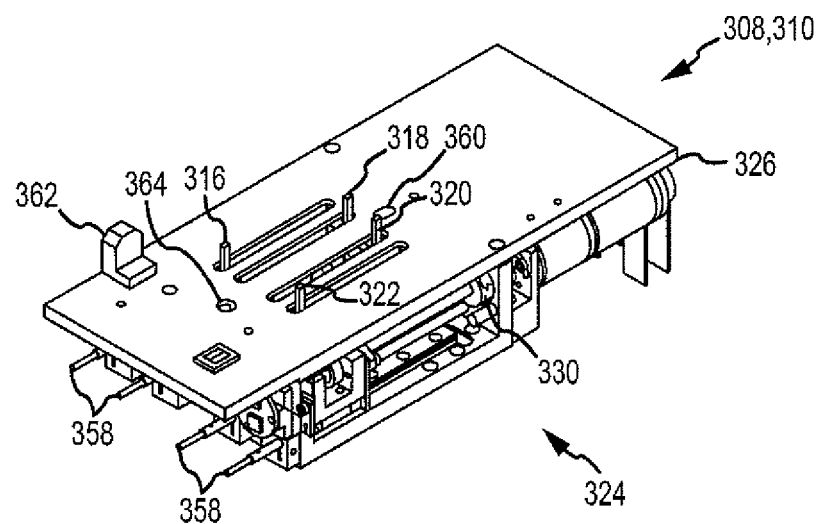
FIGS. 4a-4c are isometric views showing a sheath manipulation base of FIGS. 3a-3b in greater detail.
Figure 4B:
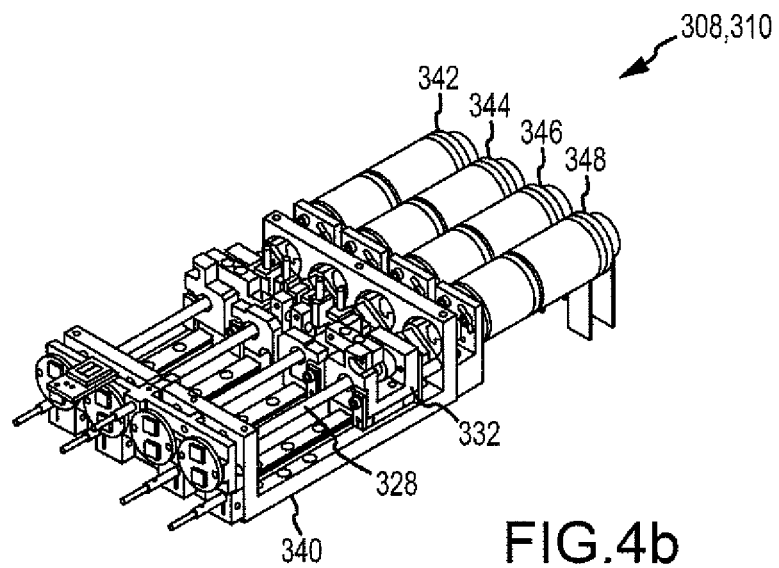
Figure 4C:
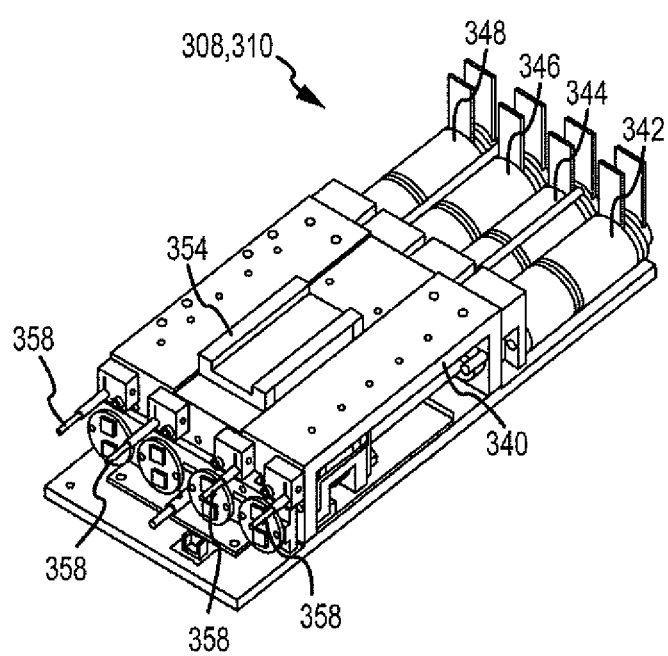
Figure 5A:
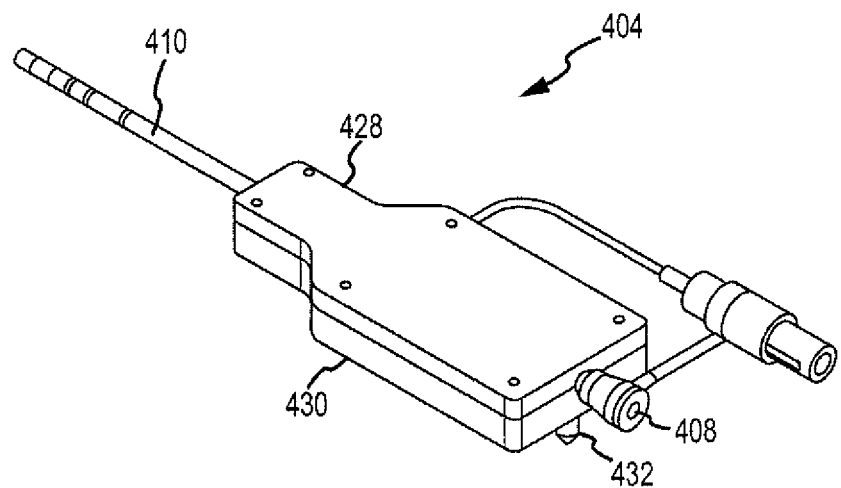
FIGS. 5a-5b are isometric views showing a sheath cartridge of FIGS. 3a-3b in greater detail.
Figure 5B:
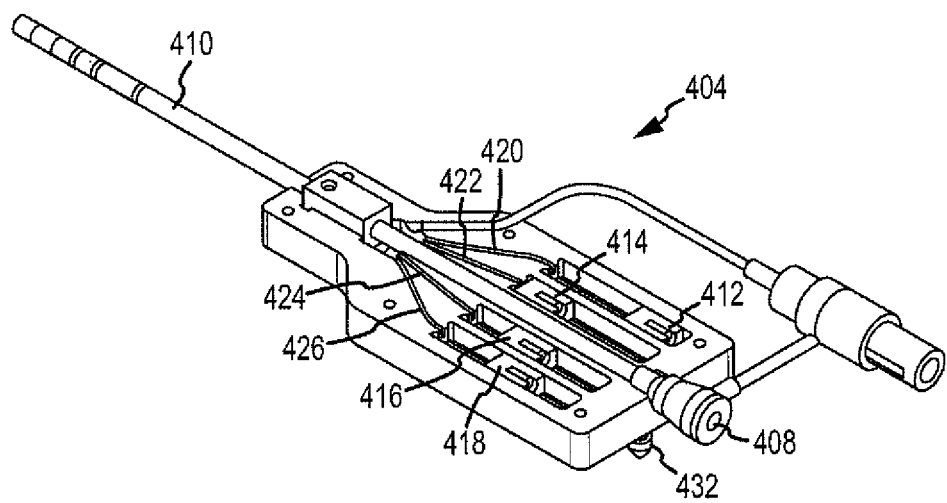

In the Figures to follow, FIGS. 3a-3b will show a manipulator assembly, FIGS. 4a-4c will show a manipulation base, and FIGS. 5a-5b will show a device cartridge.

FIG. 3a is an isometric view, with portions omitted for clarity, of manipulator assembly 302. Assembly 302 includes a catheter manipulator mechanism 304, a sheath manipulator mechanism 306, a catheter manipulation base 308, a sheath manipulation base 310, a first (catheter) drive mechanism 312, a second (sheath) drive mechanism 314, and a track 356. As further shown, assembly 302 further includes a catheter cartridge 402 and a sheath cartridge 404, with a catheter 406 having a proximal end opening 408 coupled to the catheter cartridge 402 and a sheath 410 coupled to the sheath cartridge 404.

Catheter and sheath manipulator mechanisms 304, 306 are configured to manipulate the several different movements of the catheter 406 and the sheath 410. First, each mechanism 304, 306 is configured to impart translation movement to the catheter 406 and the sheath 410. Translation movement here refers to the independent advancement and retraction (withdrawal) as shown generally in the directions designated D1 and D2 in FIG. 3a. Second, each mechanism 304, 306 is also configured to effect deflection of the distal end of either or both of the catheter and sheath 406, 410. Third, each mechanism 304, 306 can be operative to effect a so-called virtual (omni-directional) rotation of the distal end portion of the catheter 406 and the sheath 410. Virtual rotation, for example, can be made through the use of independent four-wire steering control for each device (e.g., eight total steering wires, comprising four sheath control wires and four catheter control wires). The distal end movement is referred to as "virtual" rotation because the outer surface of the sheath (or catheter) does not in fact rotate in the conventional sense (i.e., about a longitudinal axis) but rather achieves the same movements as conventional uni-planar deflection coupled with axial rotation. In addition to the present description of virtual rotation, further details can be found in PCT/US2009/038597 entitled "ROBOTIC CATHETER SYSTEM WITH DYNAMIC RESPONSE", published as WO 2009/120982.

Each manipulator mechanism 304, 306 further includes a respective manipulation base 308, 310 onto which are received catheter and sheath cartridges 402, 404. Each interlocking base 308, 310 can be capable of travel in the longitudinal direction of the catheter/sheath (i.e., D1, D2 respectively) along a track 356. In an embodiment, D1 and D2 can each represent a translation of approximately 8 linear inches. Each interlocking base 308, 310 can be translated by a respective high precision drive mechanism 312, 314. Such drive mechanisms can include, for example and without limitation, an electric motor driven lead screw or ball screw.

The manipulator mechanisms 304, 306 are aligned with each other such that catheter 406 can pass through sheath 410 in a coaxial arrangement. Thus, sheath 410 can include a water-tight proximal sheath opening 408. Overall, the manipulator mechanisms 304, 306 are configured to allow not only coordinated movement but also relative movement between catheter and sheath cartridges 402, 404 (and thus relative movement between catheter and sheath).

FIG. 3b is an isometric view of manipulator assembly 302, substantially the same as FIG. 3a except that catheter and sheath cartridges 402, 404 are omitted (as well as catheter and sheath 406, 410) so as to reveal an exposed face of the manipulation bases 308, 310.

FIG. 4a is an isometric, enlarged view showing manipulation base 308 (and base 310) in greater detail. Each cartridge 402, 404 has an associated manipulation base 308, 310. Each base 308, 310 can include a plurality of fingers 316, 318, 320 and 322 (e.g., one per steering wire) that extend or protrude upwardly to contact and interact with steering wire slider blocks (i.e., such as slider blocks 412, 414, 416, 418 are best shown in FIG. 5b) to independently tension select steering wires 420, 422, 424, 426 (also best shown in FIG. 5b). Each finger can be configured to be independently actuated (i.e., moved back and forth within the oval slots depicted in FIG. 4a) by a respective precision drive mechanism, such as a motor driven ball screw 324. A plate 326 provides a surface onto which one of the cartridges 402, 404 are seated.

FIG. 4b is an isometric, enlarged view of base 308 (and base 310), substantially the same as FIG. 4a except with plate 326 omitted. Each motor-driven ball screw 324 (best shown in FIG. 4a, i.e., for both finger control and for cartridge translation control, can further include encoders to measure a relative and/or an absolute position of each element of the system. Moreover, each motor-driven ball screw 324 (i.e., for both finger control and cartridge translation control) can be outfitted with steering wire force sensors to measure a corresponding steering wire tension. For example, a corresponding finger 316, 318, 320 or 322 can be mounted adjacent to a strain gauge for measuring the corresponding steering wire tension. Each motor-driven ball screw 324 can include a number of components, for example only, a rotary electric motor (e.g., motors 342, 344, 346 and 348), a lead screw 328, a bearing 330 and a coupler 332 mounted relative to and engaging a frame 340. In the depicted embodiments linear actuation is primarily, if not exclusively, employed. However, some known examples of systems with rotary-based device drivers include U.S. application Ser. No. 12/150,110, filed 23 Apr. 2008 (the '110 application); and U.S. application Ser. No. 12/032,639, filed 15 Feb. 2008 (the '639 application). The '110 application and the '639 application are hereby incorporated by reference in their entirety as though fully set forth herein. These and other types of remote actuation can directly benefit from the teaching of the instant disclosure.

FIG. 4c is an isometric, enlarged view of base 308 (and base 310) that is taken from an opposite side as compared to FIGS. 4a-4b. Bases 308, 310 can include components such as a plurality of electrically-operated motors 342, 344, 346 and 348, respectively coupled to fingers 316, 318, 320 and 322. A bearing 354 can be provided to facilitate the sliding of bases 308, 310 on and along track 356. A plurality of inductive sensors (e.g. home sensors) 358 can also be provided for guiding each manipulation base to a home position.

FIG. 5a is an isometric, enlarged view showing, in greater detail, sheath cartridge 404. It should be understood that the description of sheath cartridge 404, except as otherwise stated, applies equally to catheter cartridge 402. Catheter 406 and sheath 410 can be substantially connected or affixed to respective cartridges 402, 404 (e.g., in the neck portion). Thus, advancement of cartridge 404 correspondingly advances the sheath 410 and retraction of cartridge 404 retracts the sheath 410. Likewise, although not shown, advancement of cartridge 402 correspondingly advances catheter 406 while a retraction of cartridge 402 retracts catheter 406. As shown, sheath cartridge 404 includes upper and lower cartridge sections 428, 430.

FIG. 5b is an isometric, enlarged view showing, in greater detail, sheath cartridge 404, with upper section 428 omitted to reveal interior components. Cartridge 404 can include slider blocks (e.g., as shown for cartridge 404, slider blocks 412, 414, 416, 418), each rigidly and independently coupled to a respective one of a plurality of steering wires (e.g., sheath steering wires 420, 422, 424, 426) in a manner that permits independent tensioning of each steering wire. Likewise, cartridge 402 for catheter 406 also includes slider blocks for coupling to a plurality (i.e., four) steering wires. Device cartridges 402, 404 can be provided as a disposable item that is capable of being easily positioned (e.g., snapped) into place (i.e., onto a respective base 408, 410). Sheath cartridge 404 can be designed in a similar manner as the catheter cartridge 402, but will typically be configured to provide for the passage of catheter 406.

Referring to FIGS. 4a and 5a, catheter and sheath cartridges 402, 404 are configured to be secured or locked down onto respective manipulation bases 308, 310. To couple cartridge 402 (and 404) with base 308 (and 310), one or more locking pins (e.g., 432 in FIG. 5a) on the cartridge can engage one or more mating recesses 360 in the base (see FIG. 4a). In an embodiment, such recesses 360 can include an interference lock such as a spring detent or other locking means. In an embodiment, such other locking means can include a physical interference that can require affirmative/positive action by the user to release the cartridge. Such action can include or require actuation of a release lever 362. Additionally, the cartridge can include one or more locator pins (not shown) configured to passively fit into mating holes on the base (e.g., 364 in FIG. 4a).

In operation, a user first manually positions catheter 406 and sheath 410 (with catheter 406 inserted in sheath 410) within the vasculature of a patient. Once the medical devices are roughly positioned in relation to the heart or other anatomical site of interest, the user can then engage or connect (e.g., "snap-in") the catheter and sheath cartridges into place on respective bases 308, 310. When a cartridge is interconnected with a base, the fingers fit into the recesses formed in the slider blocks. For example, with respect to the sheath cartridge 404 and sheath base 310, each of the plurality of fingers 316, 318, 320 or 322 fit into corresponding recesses formed between the distal edge of slider blocks 412, 414, 416, 418 and a lower portion of the cartridge housing (best shown in FIG. 5b). Each finger can be designed to be actuated in a proximal direction to respectively move each slider block, thereby placing the respective steering wire in tension (i.e., a "pull" wire). Translation, distal end bending and virtual rotation can be accomplished through the use of the RCGS 10.

Figure 6:
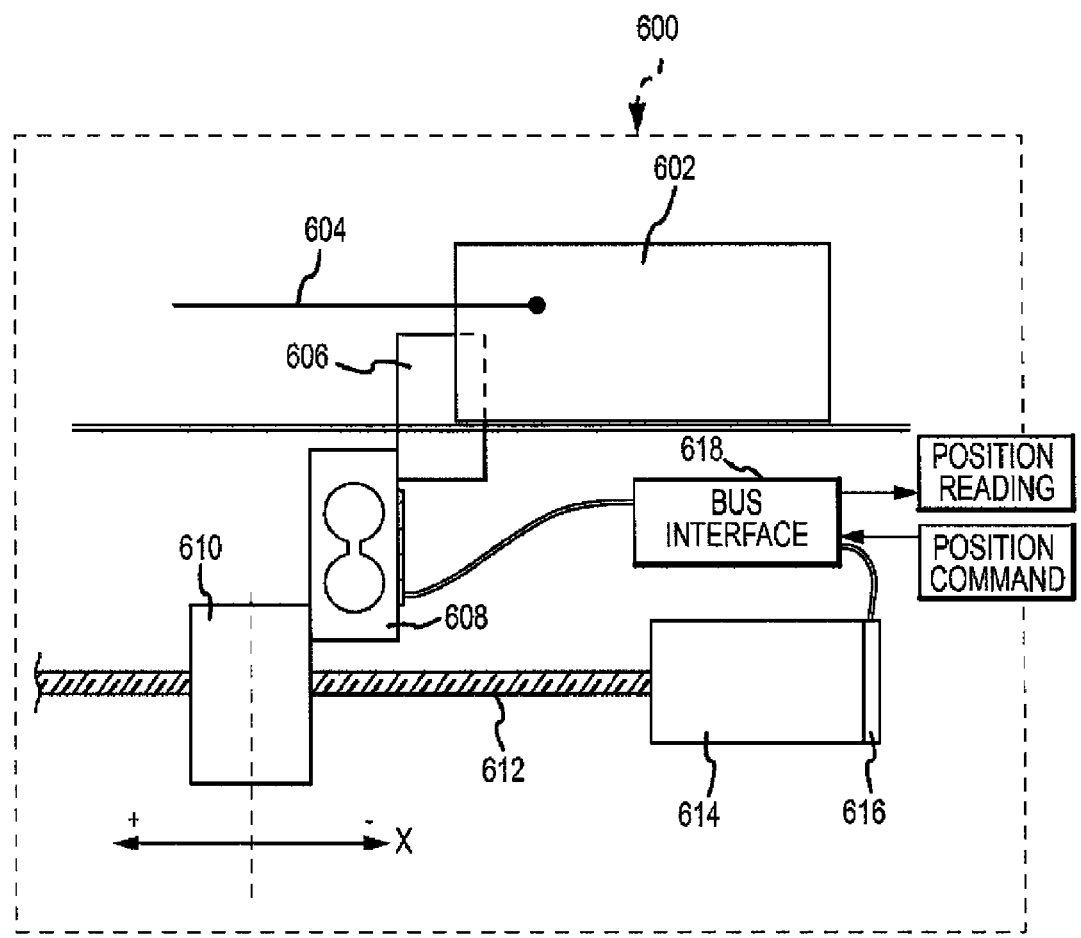
FIG. 6 is a diagrammatic view of the sheath manipulation mechanism of FIG. 2.

FIG. 6 is a diagrammatic view of a node suitable for connection to a communications bus (not shown) in RCGS 10. The node includes an actuation unit 600, similar to the actuation mechanisms described above (e.g., catheter actuation mechanism 304). The RCGS 10 can have at least ten such actuation units (i.e., one for each of the four catheter steering wires, four sheath steering wires, one catheter manipulation base and one sheath manipulation base), which as described include electric motors. The diagnostic logic of the present disclosure is configured to monitor all the electric motors to detect runaway motor fault conditions.

FIG. 6 shows in diagrammatic or block form many of the components described above—where appropriate, references to the earlier describe components will be made. Actuation unit 600 includes a first, slidable control member 602 (i.e., slider as described above) that is connected to or coupled with a second, tensile control member 604 (i.e., steering wire as described above). The slider 602 can be configured to interface with a third, movable control member 606 (i.e., finger as described above). The finger 606 can further be operatively coupled with a portion of a sensor 608 (e.g., a force sensor), which, in turn, can be coupled with a translatable drive element 610 that can be mechanically moved. For example, without limitation, translatable drive element 610 can ride on or can otherwise be mechanically moved by a mechanical movement device 612 that, in turn, can be coupled with an electric motor 614. The mechanical movement device 612 can comprise a lead screw while the translatable drive element 610 can comprise a threaded nut, which can be controllably translated by screw 612 in the X+ or X− directions. In another embodiment, mechanical movement device 612 can include a ball screw, while translatable drive element 610 can include a ball assembly. Many variations are possible, as will be appreciated by one of ordinary skill in the art.

The actuation unit 600 also includes a rotary motor position encoder 616 that is coupled to the motor 614 and is configured to output a signal indicative of the position of the motor 614. The encoder 616 can comprise an internal, optical encoder assembly, integral with motor 614, configured to produce a relatively high accuracy output. The motor position sensor can operate in either absolute or relative coordinates. In an embodiment, a second motor position sensor (not shown) can also be provided, such as a potentiometer (or impedance-based), configured to provide a varying voltage output proportional to the motor's rotary position. The output of the secondary position sensor can be used as an integrity check of the operating performance of the primary position sensor (encoder) during start-up or initialization of the actuation unit.

Actuation unit 600 also includes one or more local controllers including a bus interface 618 to facilitate exchange of information between actuation unit 600 and electronic control system 200 (via the bus). The controller communicates with the main electronic control system 200 via the bus interface and is configured, among other things, to (1) receive and execute motor actuation commands issued by the electronic control system 200 for controlling the movements of motor 614; and (2) receive and execute a command (issued by the electronic control system 200) to take a motor position sensor reading, for example, from encoder 616 and subsequently report the reading to system 200. As described herein, commands from the monitoring, managing and protecting system 700 based on information obtained at non-targeted tissue and sent via (or independent of) the electronic control system 200, can be used to stop a medical procedure or modify the procedure in such a way to protect the non-targeted tissue from damage or from additional damage.

Figure 7:
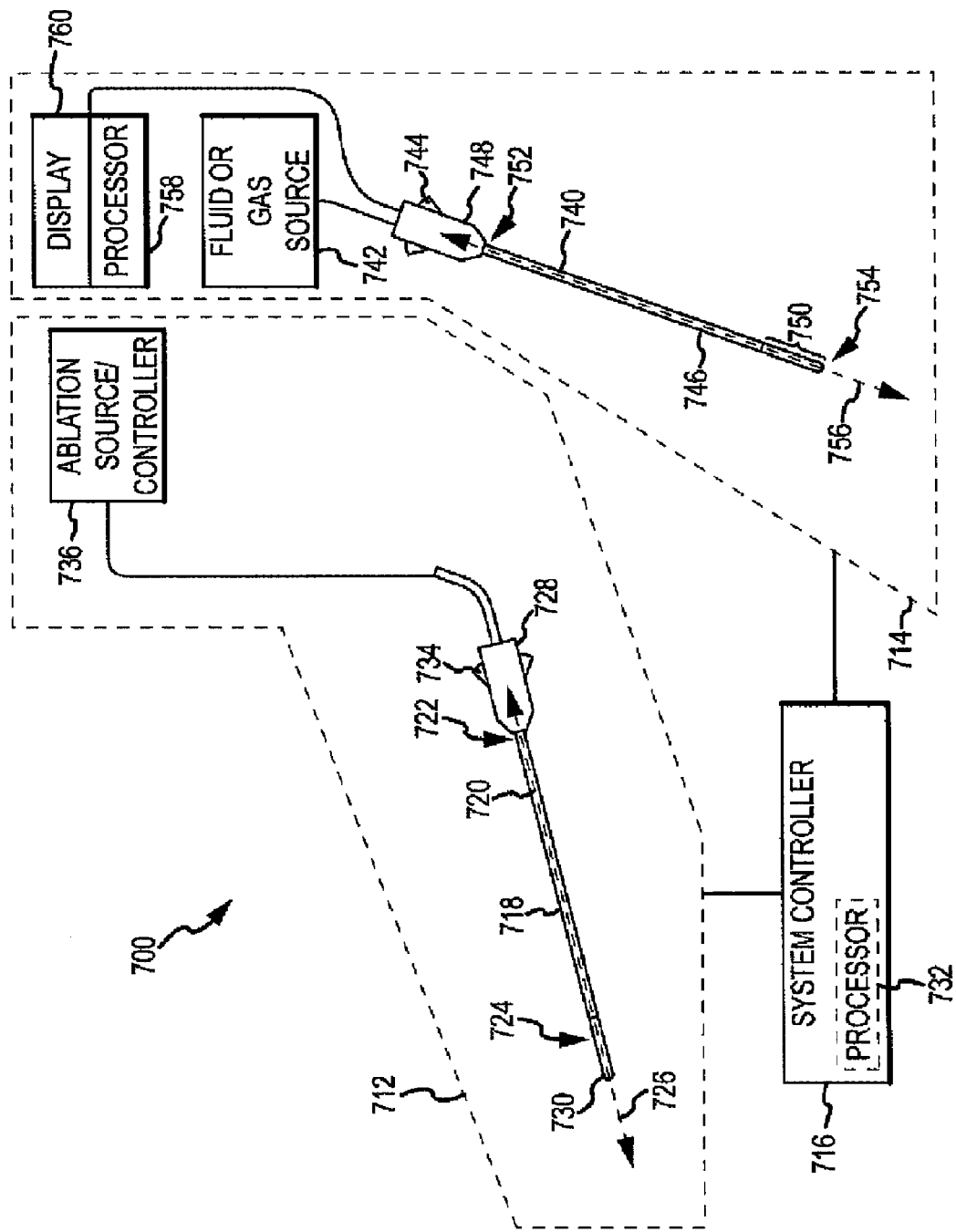
FIG. 7 is a functional block diagram of an exemplary embodiment of a system for performing a medical procedure, such as an ablation, and for monitoring, managing and/or protecting proximate non-targeted tissue during the procedure, in accordance with the present disclosure.

FIG. 7 illustrates an exemplary embodiment of a monitoring, managing and protecting system 700 for use at non-targeted tissue proximate a medical procedure, such as an ablation procedure. As described herein, the system 700 monitors, manages, and/or protects non-targeted tissue proximate an ablation site during the ablation procedure by obtaining electrical information pertaining to non-targeted tissue and determining if the information indicates that the non-targeted tissue is being or will be damaged by the ablation device or the ablation procedure.

As shown in FIG. 7, the exemplary monitoring, managing and protecting system 700 is configured to manage, modify and/or stop the energy being emitted from an ablation catheter through and using an electrical response assessment system or system controller 716. Monitoring, managing and/or protecting non-targeted tissue during a medical procedure can also be accomplished using the electronic control system 200 of the RCGS 10 (see FIG. 1) to control the ablation procedure when certain electrical characteristics are detected. The monitoring, managing and protecting system 700 can also work independently from the RCGS 10 by providing visual, audible or haptic information so that the practitioner can manually modify or stop the procedure before any damage or further damage is done to the non-targeted tissue.

FIG. 7 illustrates the monitoring, managing and protecting system 700 working in conjunction with an ablation subsystem 712, a monitoring, managing and/or protecting subsystem 714, and, in an exemplary embodiment, a system controller 716 (such as an electrical response assessment system), including one or more processors 732, connected to each of the ablation subsystem 712 and the monitoring, managing and protecting subsystem 714. The ablation subsystem 712 is generally a component of or operatively coupled to the manipulator assembly 300 and/or the device cartridge 400 of the RCGS 10 described above, as is generally known in the art (see, for example, U.S. Pat. No. 6,635,054 entitled "Thermal Treatment Methods and Apparatus with Focused Energy Application," U.S. Patent Publication No. 2004/0176757 entitled "Cardiac Ablation Devices," and International Publication No. WO 2005/102199 entitled "Ablation Devices with Sensor Structures", the disclosures of which are hereby incorporated by reference in their entireties).

In an exemplary embodiment, the ablation subsystem 712 includes an ablating device 718, comprised, in part, of at least one ablation element 730 coupled to an elongate and typically flexible shaft 720 having a proximal end 722, a distal end 724, and a longitudinal axis 726 extending from the proximal end 722 through the distal end 724. As will be described in greater detail below, the ablating device 718 further includes a handle 728 coupled to the elongate shaft 720 at the proximal end 722 thereof, and the at least one ablation element 730 is mounted to the elongate shaft 720 at or near the distal end 724 thereof. While it should be understood that the ablating device 718 may include one or more ablation elements 730, and that ablating devices 718 having more than one ablation elements 730 are within the spirit and scope of the present disclosure, for ease of description purposes only, the description below will be limited to an embodiment wherein the ablating device 718 includes a single ablation element 730.

The flexible elongate shaft 720 may be formed of any number of materials, such as, for example and without limitation, PEBAX®, Nylon, and polyurethane. In another exemplary embodiment, the elongate shaft 720 is constructed of, or incorporates, a metal wire braid, as is known in the art. The elongate shaft 720 further includes at least one, and typically multiple, inner passageways or lumens (not shown) disposed therein. The lumens extend longitudinally along an axial portion of the shaft 720 from the proximal end 722 to the distal end 724, and are configured to have one or more components of the ablating device 718 disposed therein, such as, for example and without limitation, pull wires, planarity wires, fluid irrigation or drainage lumens, lead wires for the ablation element 730, a rotation wire, or, as will be described in greater detail below, components required for inflating and deflating balloons with, for example, fluid, gas, and/or extruding gels, associated with the ablating device 718, and the ablation element 730, in particular.

As briefly described above, the handle 728 of the ablating device 718 is disposed at the proximal end 722 of the elongate shaft 720. The handle 728 is operative to, among other things, effect movement of the shaft 720 (i.e., steer the ablating device 718), and/or selectively manipulate the distal end 724 of the elongate shaft 720 to position the distal end 724, and therefore, the at least one ablation element 730, in a desired location when the ablating device 718 is disposed within a patient. More particularly, in one embodiment provided for exemplary purposes only, one or more pull wire(s) (not shown) are coupled to and between both the distal end 724 of the elongate shaft 720 and an actuator(s) 734 located on the handle 728. As the actuator 734 is manipulated, the corresponding pull wire(s) is caused to be pushed and pulled, for example, to effect movement, such as bending deflection, of the distal end 724 of the elongate shaft 720. It should be noted, however, that while only this particular method or technique of steering or effecting movement of the elongate shaft 720, and/or the distal end 724 thereof, is described in detail herein, the present invention is not meant to be so limited. Rather, those of ordinary skill in the art will appreciate that other methodologies or techniques of steering and/or manipulating ablating devices exist that remain within the spirit and scope of the present invention.

In addition to actuator 734, other components may also be disposed within the handle 728. For example, electrical matching circuits to electrically impedance-match the components of the ablation element 730 to an ablation energy generator or power source, or other components of the ablation subsystem 712, for example, may be disposed within the handle 728. The ablation element 730 and the energy generator can be configured to deliver one or more types of ablation energy (e.g., high intensity focused ultrasound, or HIFU, radiofrequency, laser, microwave and the like). Further, as described in detail above, an exemplary RCGS 10 can be used in conjunction with, or instead of a handle 728, to position and/or control the elongate shaft 720 and the ablation element 730 before and during an ablation procedure.

The ablation subsystem 712 further includes an energy or ablation power source 736, which is electrically connected to the ablation element 730 by electrical leads or wires (not shown) that are disposed within one or more of the lumens in the elongate shaft 720, and that extend through to the proximal end 722 thereof. When the ablation power source 736 is activated, the ablation element 730 emits an ablation energy for use during the ablation procedure.

The monitoring, managing and/or protecting subsystem 714 of system 700 will now be described. In an exemplary embodiment, the monitoring, managing and/or protecting subsystem 714 includes a protective probe 740, a fluid or gas source 742, and an actuator 744.

The protective probe 740 includes an elongate shaft 746, a handle 748, and a monitoring electrode 750. As with the shaft 720 described above, the elongate shaft 746 has a proximal end 752, a distal end 754, and a longitudinal axis 756 extending from the proximal end 752 through the distal end 754. The handle 748 is disposed at the proximal end 752 and, as described above with respect to the handle 748, may be configured, among other things, to steer or manipulate portions of the probe 740 as it is inserted into the anatomy of a patient, such as, for example, the esophagus. In an exemplary embodiment, the probe 740 is directly inserted into the esophagus such as through the mouth or sinus. However, in another exemplary embodiment, the probe 740 is introduced into the esophagus through an introducer-lumen already in place. The monitoring electrode 750 of the probe 740 is disposed at or near the distal end 754 of the elongate shaft 746.

In one exemplary embodiment, the monitoring, managing and/or protecting system is configured to obtain or measure the electrical characteristics of the non-targeted tissue, and to communicate the same to a processor 758 or other circuitry associated with subsystem 714 (or to the system controller 716). The processor 758 is configured, at least in part, to compare the measured electrical characteristics of the tissue with predetermined threshold characteristics, and to provide the practitioner performing the ablation procedure an audible and or visual warning if the measured electrical characteristics approach or reach the predetermined threshold (e.g., where burning or damage to the esophageal tissue may begin). For example, the subsystem 714 may further include an alarm system controllable by, for example, the processor 758, to provide an audible and/or haptic warning that the threshold has been met or is being approached, and/or a display monitor 760 controllable by, for example, the processor 758, to display the imaged tissue, as well as a visual warning that the threshold has been met or is being approached. This information may be further communicated to the system controller 716, to ablation subsystem 712, for example, which may then cause the ablating device 718 to be turned "off" or turned "down" in order to prevent or mitigate burning in the esophageal tissue, or to a physician. The system controller 716, the ablation system 712, the physician, or any other control system may react or utilize the information to take corrective, modifying or mitigating actions, including moving system components, turning system components off or down, adjusting power, adjusting cooling, adjusting fluid flow, or terminating procedures. The detected characteristics may also be used to predict the onset of damage to the non-targeted tissue and have the system undertake preventative or warning actions, and/or to control, modify or stop the ablative energy level. In an exemplary embodiment, low energy may be delivered by the ablating device 718 for purposes of estimating how the tissue will react, e.g., how hot the esophageal tissue will get at higher ablation energy. Further, the monitoring, managing and/or protecting subsystem 714 may be incorporated into the RCGS 10 system described herein and incorporate the electronic control system 200 of the RCGS 10 to make such determinations or decisions.

Figure 8:
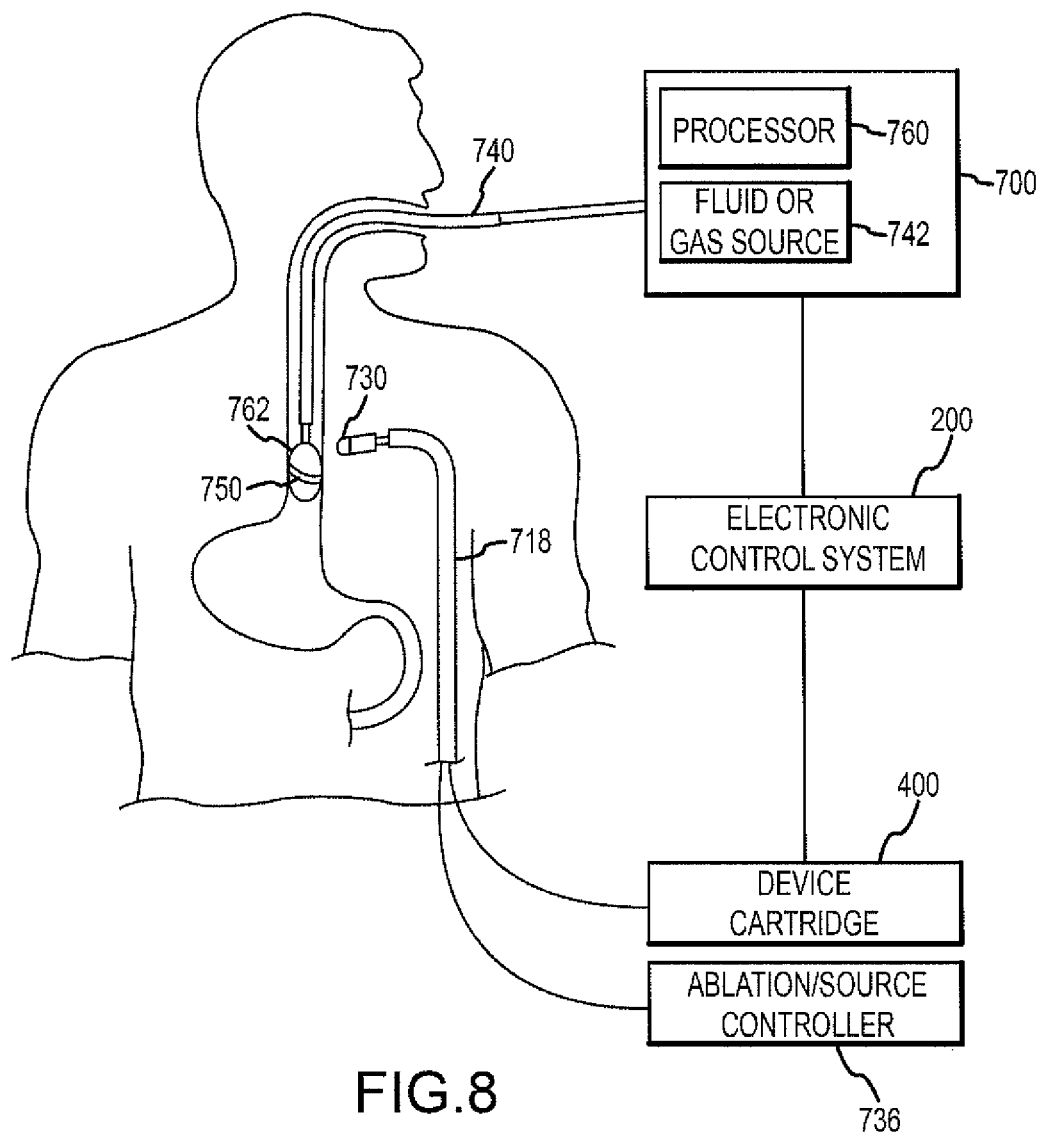
FIG. 8 is a diagrammatic and block diagram view of an exemplary embodiment of a system for performing a medical procedure, such as an ablation, and for monitoring, managing and/or protecting proximate non-targeted tissue during the procedure, in accordance with the present disclosure.

FIG. 8 is a diagrammatic and block diagram of an exemplary monitoring, managing and/or protecting system 700 including the protective probe 740 for measuring electrical characteristics of non-targeted tissue and/or of tissue located between a monitoring electrode 750 and an ablation electrode 730.

FIG. 8 illustrates an ablation device 718 including an ablation catheter 730 that emits energy for performing ablation procedures. In an exemplary embodiment, the ablation device is mechanically or automatically controlled by the device cartridge module 400, which is controlled by the electronic control system 200 of the RCGS 10 (see FIGS. 1-6). It should be understood that other means to control an ablation device 718 are contemplated, including both automatic and manual mechanisms. If ablation catheter 730 is or could wind up located in the patient near the tissue for which the ablation procedure is directed, e.g., near the posterior atrial wall, the protective probe 740 including a monitoring electrode 750 is placed into the patient such that the monitoring electrode 750 is proximate the non-targeted tissue, in this example, the anterior wall of the esophagus. The monitoring, managing and/or protecting system 700 includes a fluid or gas source 742 and a processor 760 such that the monitoring electrode 750 can be anchored proximate the ablation procedure, as described herein. For example, a balloon 762 may be used in conjunction with the monitoring electrode 750, such that once the monitoring electrode 750 is properly located, the balloon 762 can be filled with gas or liquid from the fluid or gas source 742 (controlled by the processor 760) to anchor the balloon 762 and thus the monitoring electrode 750 in the proper place. Further, the electronic control system 200 from the RCGS 10 can be utilized in conjunction with or instead of the processor 760 to accomplish the same function. As such, the electrical response assessment system 700 can stand alone or be part of the electronic control system 200. In the latter event, the electrical response assessment system 700 can receive information and/or signals from the monitoring catheter 750 and determine if the ablation catheter 730 is damaging non-targeted tissue during the medical procedure. In an exemplary embodiment, the electrical response assessment system 700 will either transmit the information and/or signals to the electronic control system 200 for determination, or the electrical response assessment system 700 can itself make a determination and indicate the dangerous condition to the electronic control system 200 or even stop the procedure from continuing.

As described herein, the electrical measurements made by the monitoring catheter 750 can be useful for assessing, for example, information on the fat layer between the endocardial wall and the esophagus and/or highly localized and instantaneous information on the progression of lesion on the posterior wall, among other information.

Further, it has been determined that one can utilize an algorithm to predict the temperature of tissue a predetermined depth below the surface, for example 3 mm, by determining certain electrical characteristics. In an exemplary embodiment, a determination of the reactance (X), the resistance (R), the impedance (Z), and the phase angle ($\phi$) components of the complex impedance between an electrode and the tissue, the instantaneous power applied to the tissue (P) at the point in time for which the calculation is made, the duration of the lesion formation process (dt), and the temperature of the tip of the catheter (T) were significant factors to be considered in an algorithm. More specifically, it has been determined that the reactance (X), resistance (R), power (P), catheter temperature (T), and impedance (Z) at the time of the calculation, the product of the power (P) and the duration (dt) of the lesion formation process, the pre-ablation change in the phase angle $\phi$ between when the electrode contacts the tissue and prior to the electrode contacting the tissue (d$\phi$) (i.e., when the electrode is in the chamber but not in contact with the tissue, for example), the natural log of the duration (dt), and the natural log of the instantaneous power (P) are the most significant factors to be considered. In addition to the description set forth herein, further details of such algorithms can be found in commonly owned U.S. patent application Ser. No. 12/946,941 entitled "SYSTEM AND METHOD FOR ASSESSING THE FORMATION OF A LESION IN TISSUE", the entire disclosure of the application being hereby incorporated by reference.

As with the depth prediction algorithm described in the reference, it was further determined that various other factors would possibly have an impact on the accuracy of the temperature prediction algorithm. These factors include, for example and without limitation, certain parameters and/or characteristics of the equipment and/or their arrangement (such as, for example, the type of catheter and ablation generator being used, the irrigation flow rate, etc.) as well as the depth below the surface (e.g., endocardial surface) of the tissue for which the temperature is being predicted. Accordingly, it was determined that for the equipment used in the testing and for a depth of three millimeters (3 mm) below the tissue surface (which is provided for exemplary purposes only) the most computationally efficient algorithm would be based on the factors above (e.g., X, R, P, T, Z, d$\phi$, dt, etc.), as well as certain predetermined coefficients and constants to account for design parameters or characteristics of the devices/equipment used in the ablation procedure, for example. More specifically, it was determined that the best equation or algorithm was the following equation (1):

$$\text{Predicted Temperature} = a + b_1 X + b_2 R + b_3 P + b_4 T + b_5 Z + b_6 (P^*(dt)) + b_7(d)\phi + b_8(\ln dt) + b_9(\ln P) \quad (1)$$

In this equation, the constant a and the coefficients $b_1$-$b_9$ are predetermined values that are intended to account for the various factors associated with, for example, the equipment used in the ablation procedure (i.e., type of catheter and/or ablation generator, irrigation flow rate, etc.). The constant and coefficients, which may be positive or negative values depending on the circumstances, can be determined in a number of ways, such as, for example, controlled experimentation or using analyses, such as, for example, a regression analysis. Once the constant and coefficients are determined, they may be stored or programmed into the electronic control unit ECU of the electronic control system 200, or a memory/storage device associated therewith or accessible thereby. Alternatively, the catheter may itself include a memory such as an EEPROM that stores numerical values for the coefficients/constant corresponding to that particular type of catheter and/or other equipment, or stores a memory address for accessing the numerical values in another memory location. The ECU of the electronic control system 200 may retrieve these values or addresses directly or indirectly and factor them into the calculation accordingly.

It should be understood that while the coefficients and constant of the particular equation above may vary depending on, among other things, the specific catheter used, the ablation generator employed, the irrigation flow rate, potentially the patient, other equipment in the system, the species being treated, the depth for which the temperature is being predicted, and the like, the value calculated using the particular equation above will always be responsive to components of the complex impedance and the RF power applied to the tissue (e.g., instantaneous power) in order to arrive at an optimal assessment of the predicted temperature of the tissue a predetermined depth below the surface thereof. It should be further noted that the constant and coefficients are determined and programmed as part of the manufacturing and/or setup process of the system, and thus, are not determined during the use of the system in accordance with its intended purpose.

By way of example and illustration, employing the experimental testing and regression analysis described above, and using a RF ablation catheter available from St. Jude Medical, Inc. under the name COOLPATH™ and a 485 kHz RF ablation generator, the best prediction of the temperature of the tissue three millimeters (3 mm) below the surface of the endocardial surface of the tissue for a system employing those particular components was determined to be the following equation (2):

$$\text{Predicted Temperature} = -557 - 2.44X - 1.37R - 6.88P + 3.05T + 3.29Z + 0.0377(P^*(dt)) + 21.1(d\phi) - 14.1(\ln dt) + 167(\ln P) \quad (2)$$

As with the lesion depth prediction algorithm described above, this was determined by bench and/or animal testing that included testing on bovine myocardium. Data was collected and a regression model was performed to come to equation (2), and the values of the constant and coefficients thereof.

As set forth in equations (1) and (2), the temperature of the tip of the catheter (T) and the pre-ablation phase angle both prior to and following the electrode contacting the tissue are evaluated in predicting the temperature of the tissue. Accordingly, the system must include components to both sense the temperature of the tip of the catheter, and sense contact, or lack thereof, between the catheter and the tissue.

With respect to the temperature of the tip of the catheter (T), in an exemplary embodiment the system includes a temperature sensor disposed at the tip of the catheter. In one exemplary embodiment; the temperature sensor comprises a thermocouple disposed at the distal end of the catheter and configured to generate an electrical signal representative of the temperature sensed at the tip of the catheter. The temperature sensor is further configured to communicate the generated signal to the ECU and/or the ablation generator. In the latter instance, the ablation generator would be configured to report the temperature to the ECU. Accordingly, the ECU and/or ablation generator is electrically connected to the sensor (i.e., either by wire(s) or wirelessly) and is configured to receive the electrical signal therefrom.

As set forth herein, the present disclosure describes a system for monitoring, managing and/or protecting non-targeted tissue during medical procedures by determining the electrical characteristics of the non-targeted tissue (or the electrical characteristics of the tissue between a monitoring probe and the probe used in the medical procedure) before and/or during the medical procedure. For exemplary purposes and for ease of understanding, the present disclosure refers to the non-targeted tissue as the tissue in the esophagus and more particularly, in the anterior wall of the esophagus. Further, for similar reasons, the medical procedure is referred to as an ablation procedure and the location of the procedure is at or proximate the posterior atrial wall. The following Figures illustrate and describe multiple embodiments of a monitoring, managing and/or protecting system of the esophagus during an ablation proceeding. The scope of the present disclosure is not to be limited to this particular embodiment, and is meant to include other non-targeted tissue proximate targeted tissue during a medical procedure, along with other medical procedures.

In order to monitor and thus control or permit the control of an ablation procedure, the monitoring catheter for monitoring the non-targeted tissue will be placed in or near the non-targeted tissue that is of concern, near the anterior wall of the esophagus. Generally, the monitoring catheter will measure the electrical characteristics of the tissue between the ablation catheter and the monitoring catheter. Such tissue may include some or all of the anterior wall of the esophagus, a fat layer, any connective tissue, and the posterior atrial wall. From these measurements as described in detail below, information on the lumped electrical properties of the tissue between the electrodes can be determined. With this information, the monitoring and protecting system can assist in the management of the medical procedure and protect the non-targeted tissue from damage or further damage.

Figure 9:
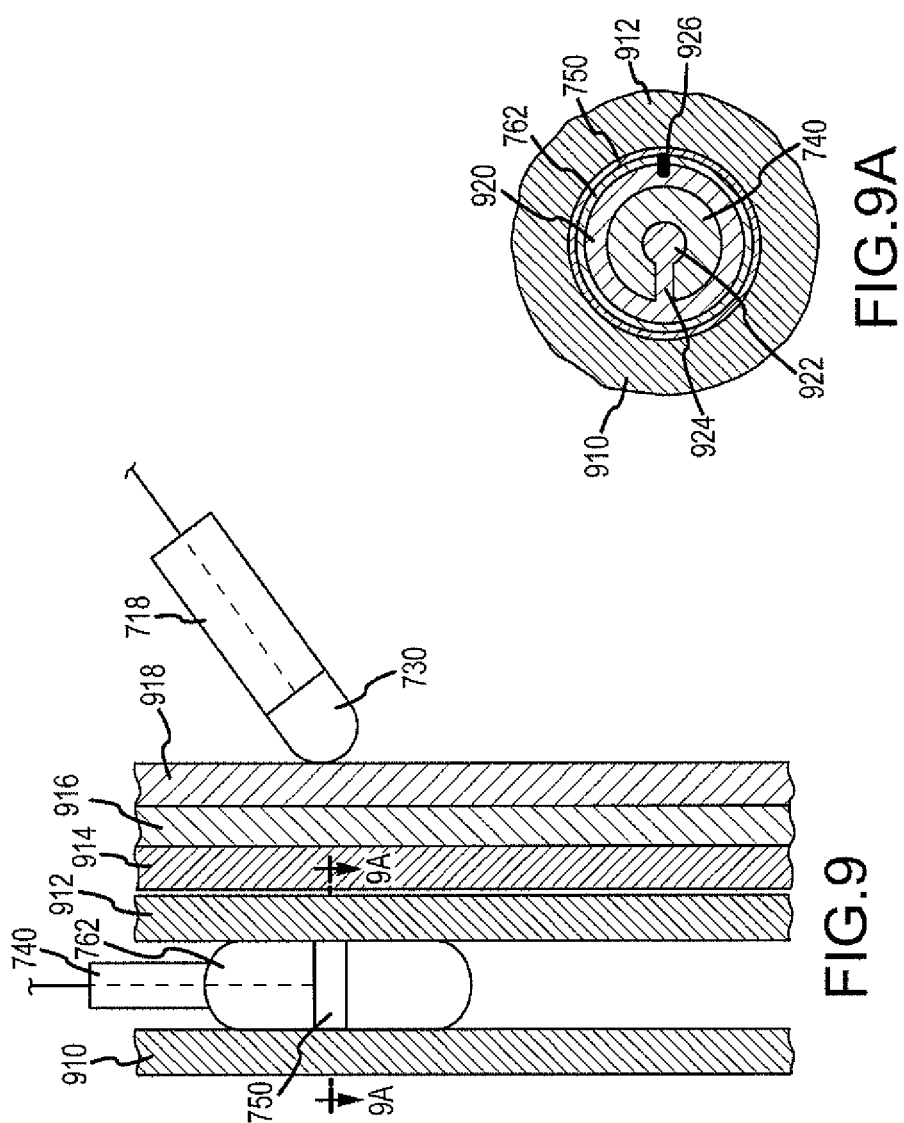
FIG. 9 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIG. 9 illustrates a partial cross-section diagrammatic view of an exemplary embodiment of the monitoring, managing and/or protecting system 700 of non-targeted tissue, wherein a monitoring probe 740 is disposed within the esophagus of a patient during a medical procedure such as an ablation, in accordance with the present disclosure. The monitoring probe 740 includes a monitoring electrode 750, in this example, a ring electrode, which is anchored in the esophagus using an inflatable and deflatable balloon 762 as described herein.

Once properly positioned in the esophagus and inflated (using the fluid or gas source 742 controlled by the processor 760 as shown in FIG. 8), the balloon 762 and monitoring electrode 750 will be positioned between the tissue of the posterior esophageal wall 910 and the tissue of the anterior esophageal wall 912. Additional tissue may include a fat layer 914, connective tissue 916 and the posterior atrial wall 918. The ablating device 718 including the ablation element or electrode 730 is placed proximate or against the posterior atrial wall 918 during the ablation procedure.

As described herein, there are a number of different inflatable/deflatable balloons or fluid based structures 762 that can be used for anchoring the monitoring electrode 750 into the proper location for monitoring the ablation procedure. Further, there are a number of other devices that can be used in conjunction with the balloon 762 or instead of the balloon 762. For example, the anchoring device can be a deflectable wire-based structure, such as an expandable/retractable spring (e.g. a coil spring, semi-elliptic spring, cantilever spring), a mesh, or a stent, or a magnetic-based structure, such as a coil (i.e. an electromagnetic coil), ferromagnet, permanent magnet, or electromagnet. Further, the monitoring electrode 750 may comprise a metal electrode, conductive fabric electrode, conductive polymer electrode, and pressure-sensitive conductive composite electrode. The monitoring electrode 750 may be a metalized film comprising part of the monitoring shaft 740 and/or the anchoring device 762, or it may be affixed to the monitoring shaft 740 and/or the anchoring device 762.

FIG. 9A is the transverse plane view of FIG. 9 as indicated. The transverse plane view illustrates the posterior esophagus wall 910 and the anterior esophagus wall 912, along with the monitoring shaft 740, monitoring electrode 750 and the anchoring balloon 762. Also shown is the fluid (or gas) 920 inside the balloon 762, the fluid lumen 922 and the orifice 924 for inflating and deflating the balloon 762 for anchoring and removing from the esophagus. The balloon 762 is operatively connected to a fluid or gas source 742 and to the processor 760 or a balloon controller (see FIG. 8). During the deployment of the balloon 762 within the esophagus, the balloon controller 760 controls the pressure of the fluid 920 that flows in and out of the balloon 762 from the fluid lumen 922 in the monitoring shaft 740 via the orifice 924 on the monitoring shaft 740. Thus, the balloon controller 760 creates and maintains a sufficient fluid pressure for safely inflating the balloon 762. When the balloon 762 is sufficiently inflated, the esophagus wall 910, 912 conforms to the shape of the balloon 762.

Also shown in FIG. 9A is an electrical sensor system interface 926 for the transmission of electrical signals and/or information from the monitoring electrode 750 to the electrical response assessment system 700. Once a determination is made that the non-targeted tissue is being damaged or might be damaged based on the information transmitted, the electrical response assessment system 700 can notify the practitioner of the dangerous situation and/or manage the medical procedure to minimize or avoid damage.

The electrical characteristics of the tissue measured by the monitoring electrode 750 and transmitted to the electrical response assessment system or component 700 may be the spatial, temporal, and/or frequency variations of the current and voltage signals within the tissue (such as an electrogram of a beating heart, signal generated from the ENSITE CONTACT™ system, and/or an ablation generator), the electrical resistance, capacitance, inductance, among others, and combinations thereof.

The measurements of the electrical characteristics of the tissue provide information on the lumped electrical properties of the tissue between the electrodes. For instance, in one application, when an endocardial electrode 730 is placed on the posterior atrial wall 918, measuring value of the complex impedance before ablation would provide information on the fat layer 914 between the endocardial wall 918 and the esophagus 912. In another application, measuring value of the complex impedance during ablation would provide highly localized and instantaneous information (that is, without the relatively and appreciably longer time constant of thermal conduction) on the progression of lesion on the posterior wall 918.

Figure 10:
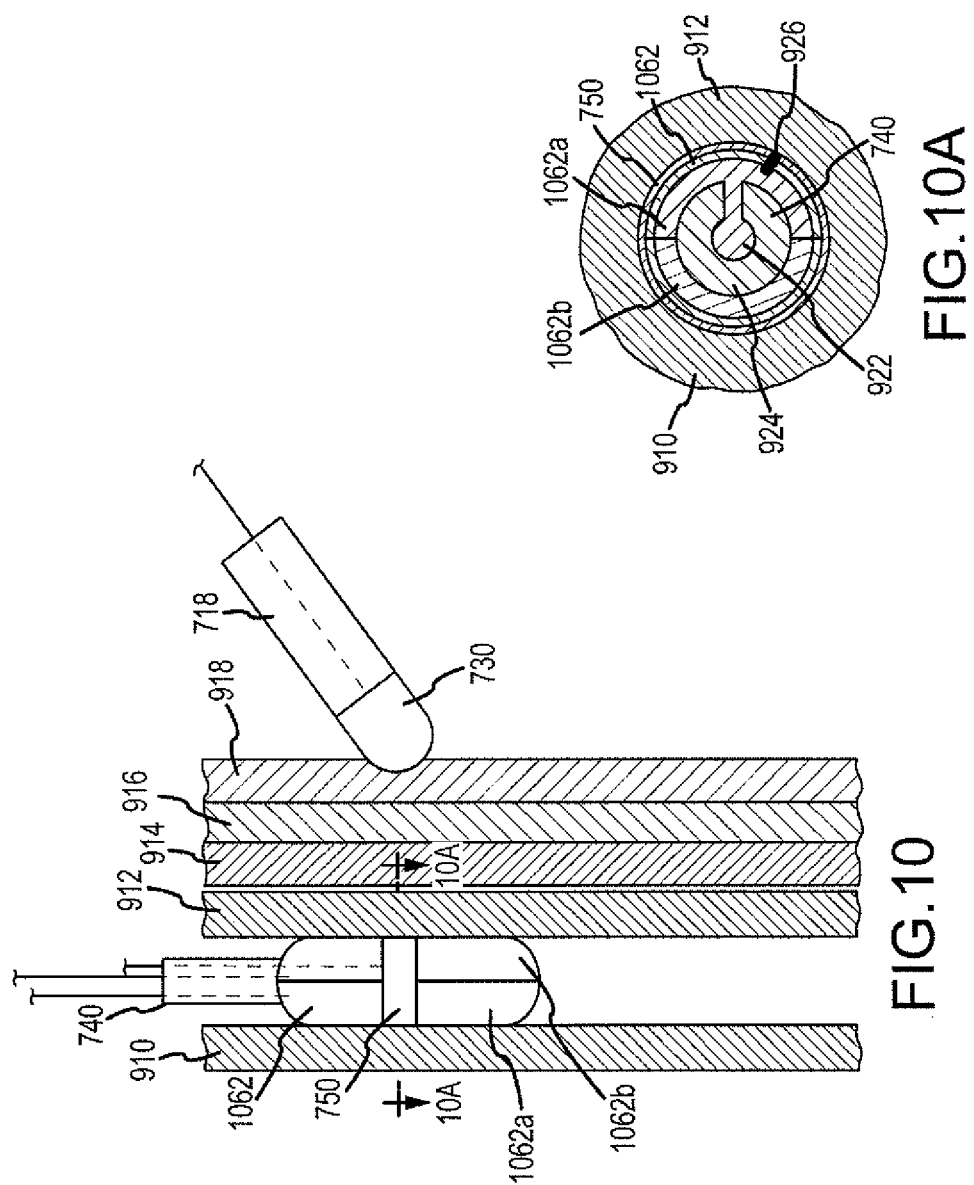
FIG. 10 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.
Figure 11:
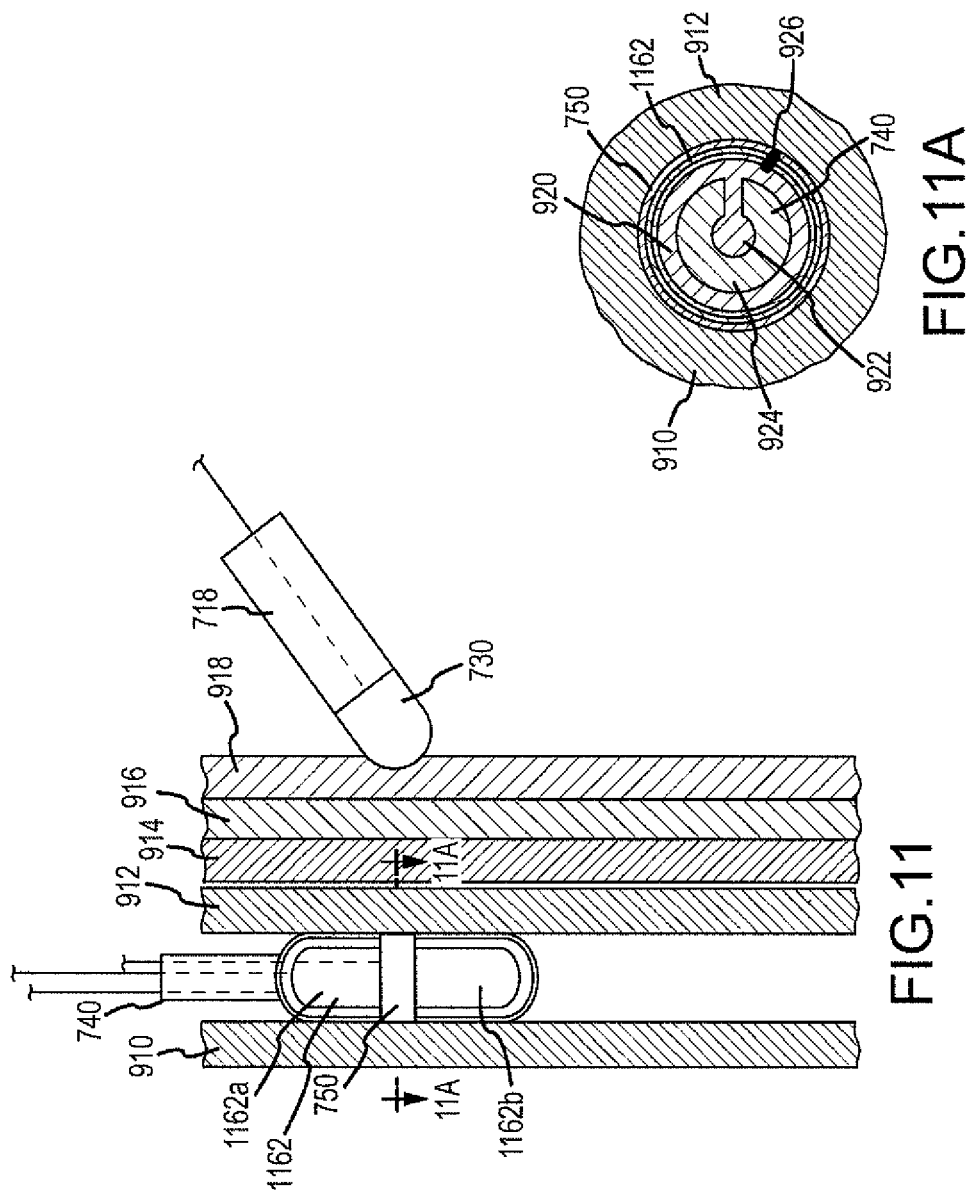
FIG. 11 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

The inflatable/deflatable balloon 762 may comprise longitudinal and/or transverse segments. FIGS. 10 and 10A show the embodiment of an inflatable/deflatable balloon 1062 comprising longitudinal segments 1062a, 1062b. FIGS. 11 and 11A show the embodiment of an inflatable/deflatable balloon comprising transverse segments 1162a, 1162b. Each segment 1162a, 1162b of the balloon 1162 may be inflated and deflated separately by the balloon controller 760. Each segment 1162a, 1162b of the balloon 1162 may comprise different fluid, such as fluids differing in thermal, electrical, magnetic, electromagnetic, optic, acoustic, and elastic properties. The wall of each balloon segment 1162a, 1162b may comprise different material, such as materials differing in thermal, electrical, magnetic, electromagnetic, optic, acoustic, and elastic properties.

The inflatable/deflatable balloon 1162 may be cooled with a cooling fluid. When the balloon 1062, 1162 comprises longitudinal 1062 and/or transverse 1162 segments, each segment 1062a, 1062b, 1162a, 1162b may be filled with different fluid and may be maintained at different temperature.

Figure 12:
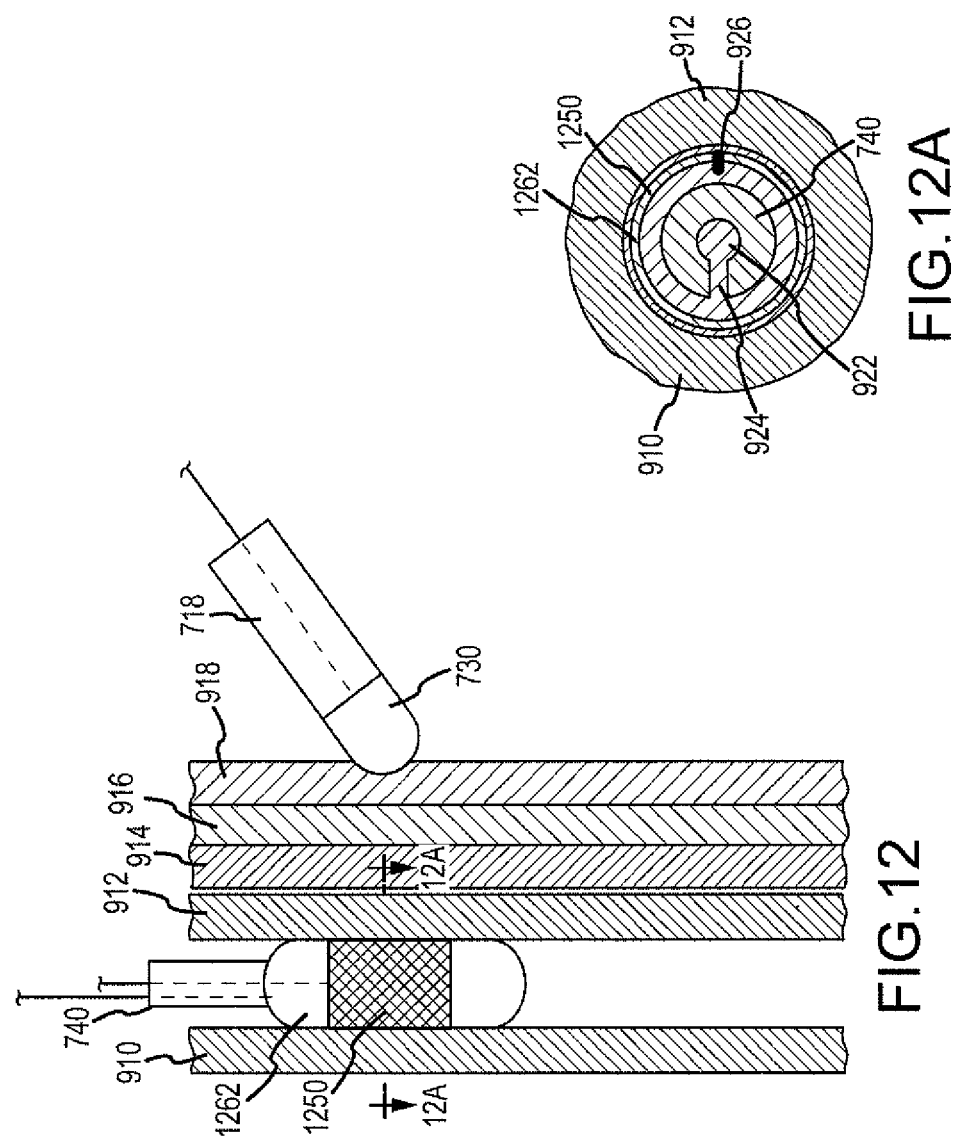
FIG. 12 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 12 and 12A show an exemplary embodiment of the monitoring, managing and/or protecting device and system 700 with a mesh electrode 1250 on an inflatable/deflatable balloon 1262. The mesh electrode 1250 may comprise material with shape memory such as Nitinol. The mesh electrode 1250 may comprise stretchable conductive material such as conductive polymer, conductive fiber, and or conductive fabric.

Figure 13:
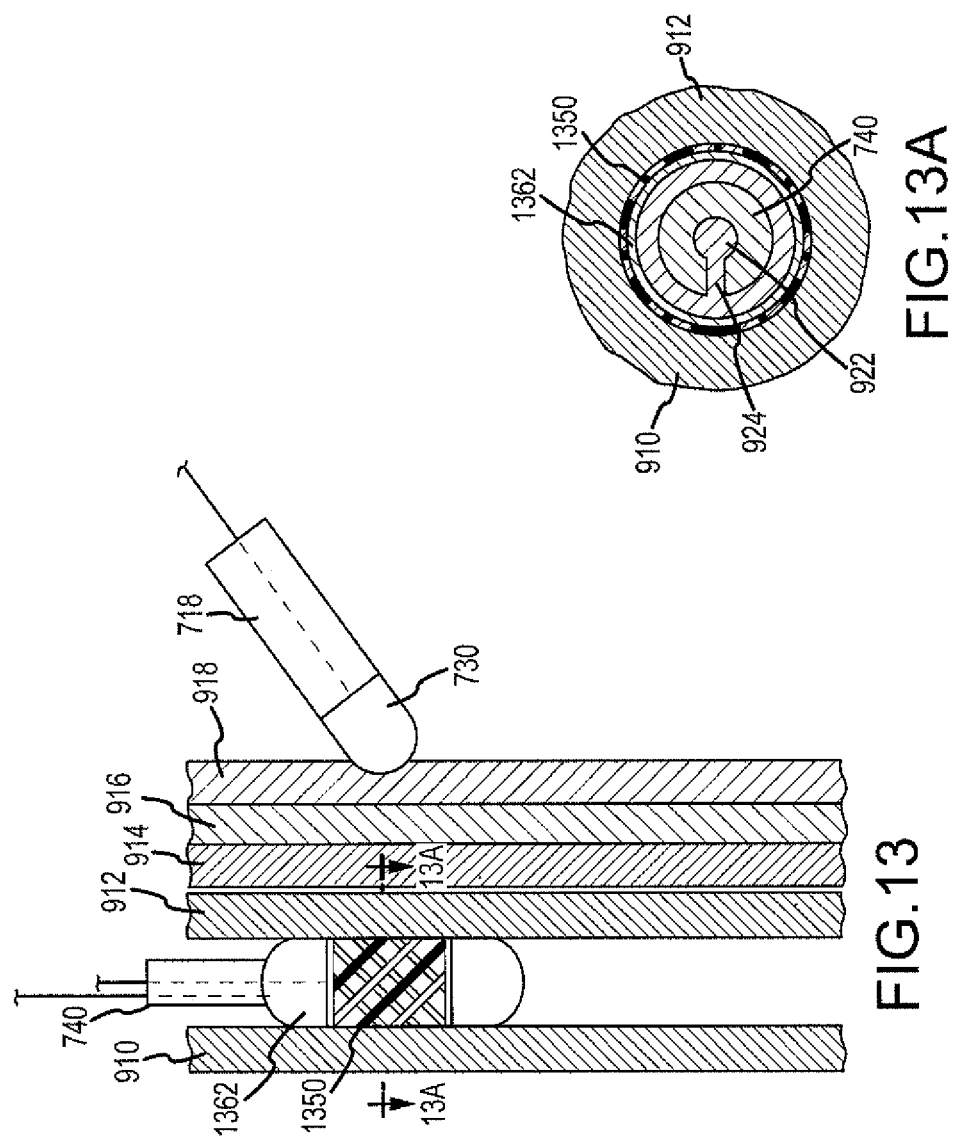
FIG. 13 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 13 and 13A show an exemplary embodiment of the monitoring, managing and/or protecting device and system 700 with a spiral electrode configured as a three-dimensional array electrode 1350 on an inflatable/deflatable balloon 1362. The array electrode 1350 may comprise electrically conductive portions on otherwise electrically insulated matrix of wires, such as the ENSITE ARRAY® Catheter. The array electrode 1350 may be affixed to the balloon 1362, and thus used in conjunction with the balloon 1362, that is, deployed in and out of the esophagus by inflating/deflating the balloon 1362.

Figure 14:
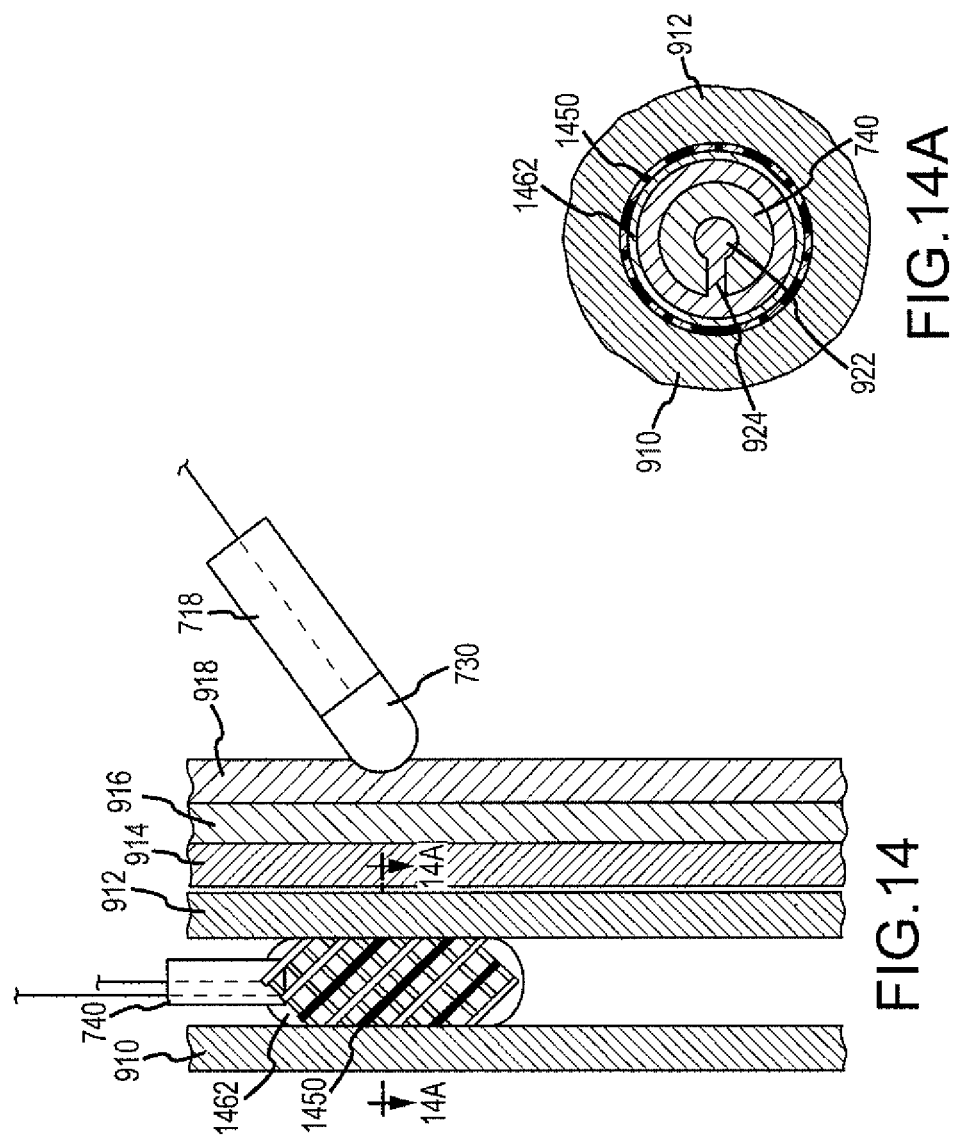
FIG. 14 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

Alternatively, as shown in FIGS. 14 and 14A, the array electrode 1450 may not be affixed to the balloon 1462. In such an embodiment, the balloon 1462 is placed within the array electrode 1450 such that the array electrode 1450 is expanded/retracted by inflating/deflating the balloon 1462 inside the array electrode 1450.

Figure 15:
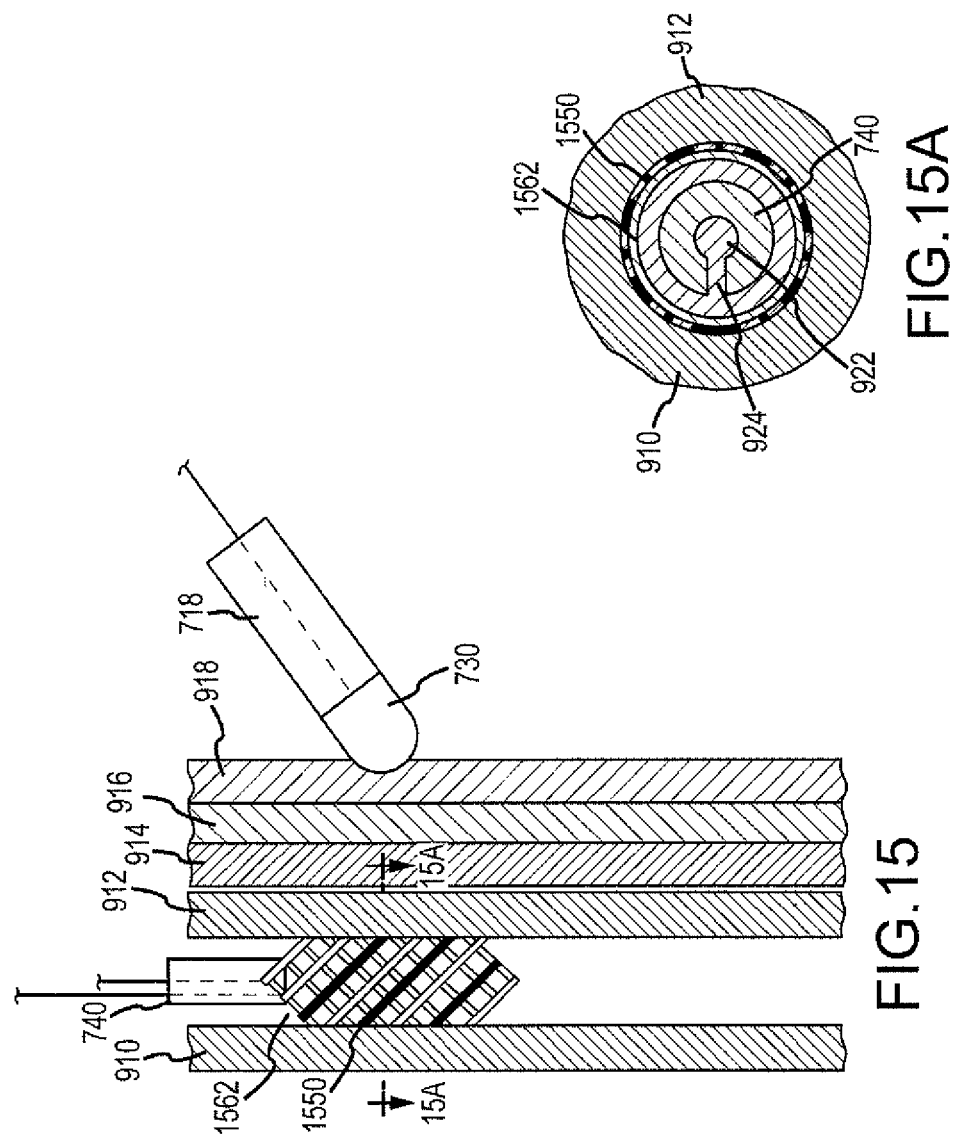
FIG. 15 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 15 and 15A show an embodiment in which the array electrode 1550 is without an inflatable/deflatable balloon. In that embodiment, the array electrode 1550 may further comprise elastic metal wires 1562 to provide structural support during deployment within the esophagus. In that configuration, the array electrode 1550 may also be used as an anchoring device 1562.

Figure 16:
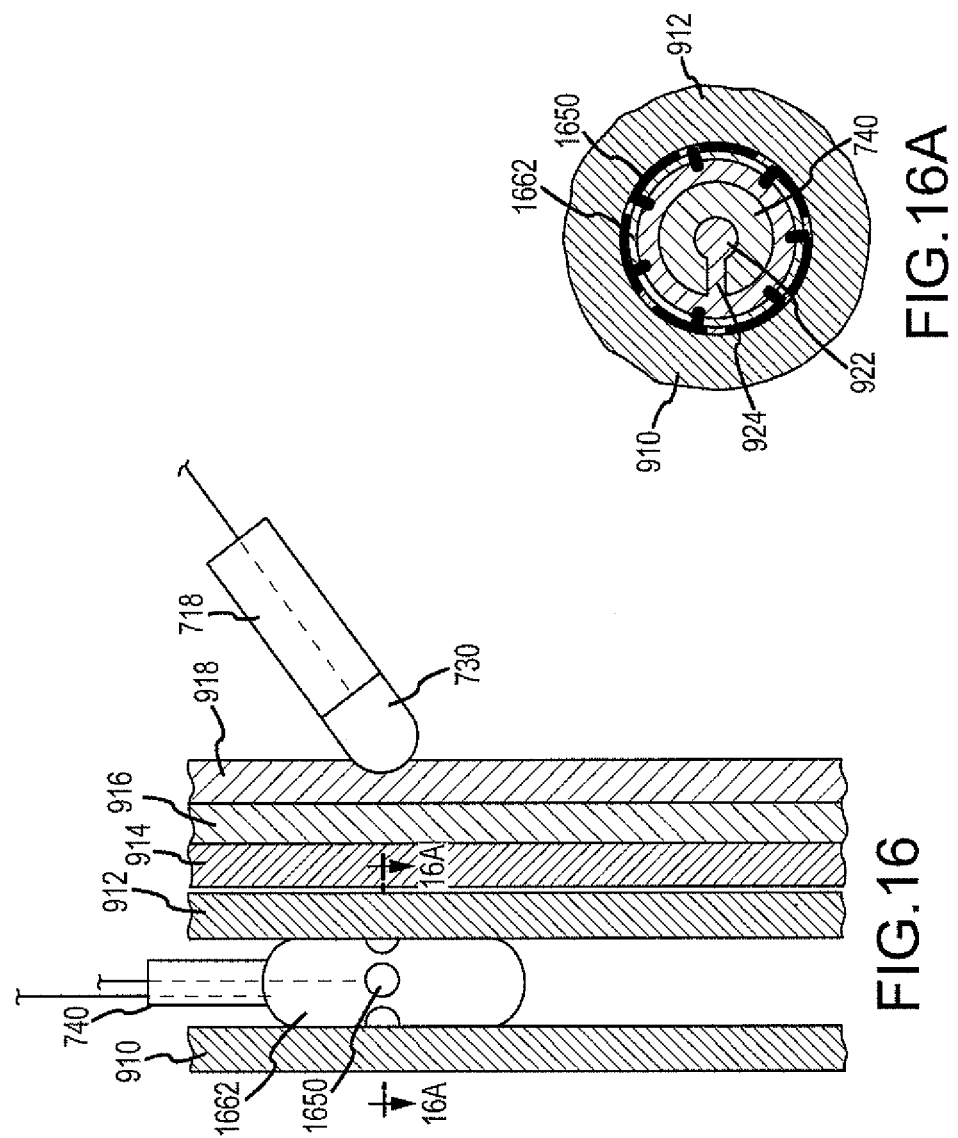
FIG. 16 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 16 and 16A show an exemplary embodiment of the monitoring, managing and/or protecting device and system 700 with esophageal spot electrodes 1650 on an inflatable/deflatable balloon 1662. The multiple spot electrodes 1650 are disposed in a plane perpendicular to a longitudinal axis of the monitoring probe 740 such that one of the spot electrodes will always be located proximate the anterior esophageal wall 912.

Figure 17:
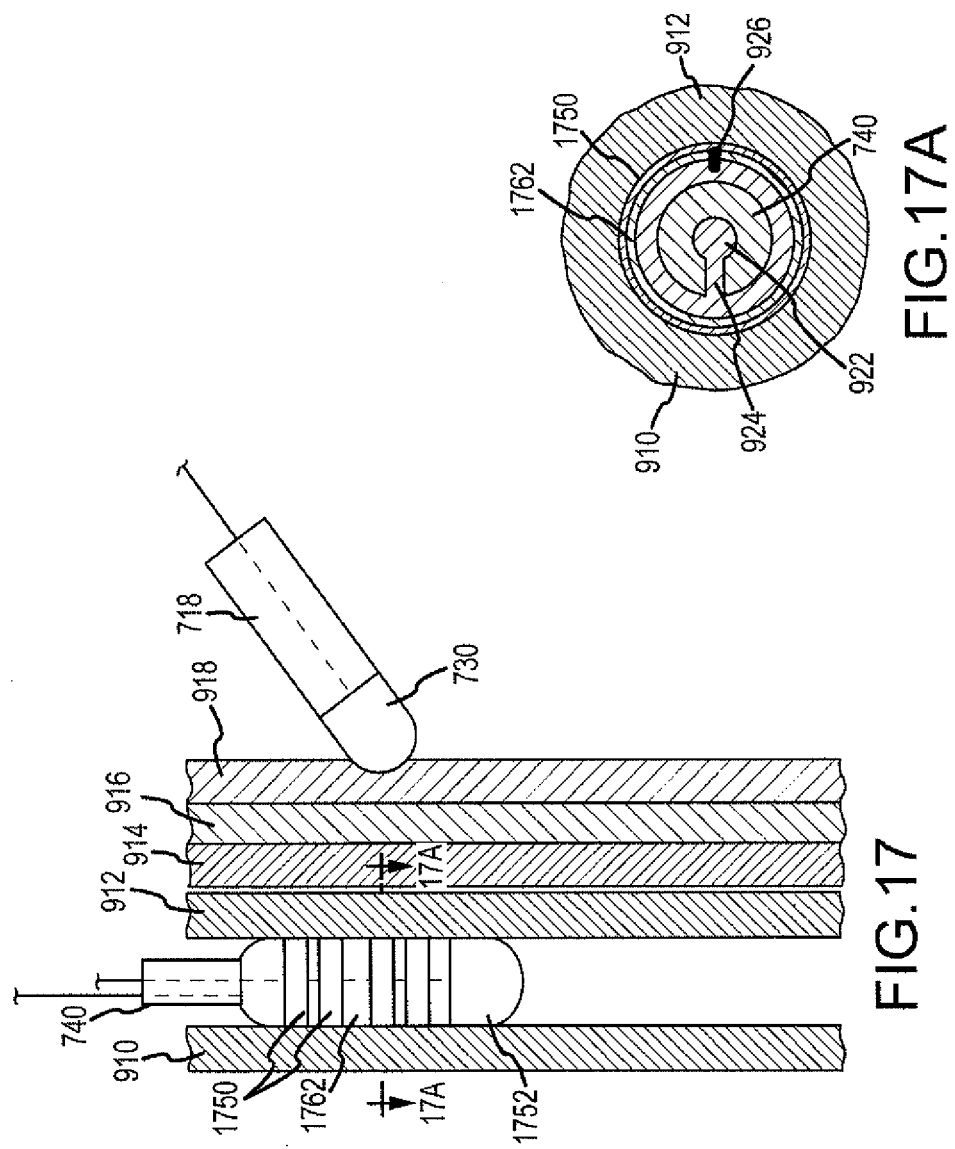
FIG. 17 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 17 and 17A show an exemplary embodiment of the monitoring, managing and/or protecting device and system 700 with distributed electrodes 1750 on an inflatable/deflatable balloon 1762. In such an embodiment, the distributed electrodes 1750 are multiple ring electrodes 1750 distributed on the surface of an inflatable/deflatable balloon 1762, and an esophageal tip electrode 1752 is located at the distal portion of the balloon 1762. The electrodes 1750, 1752 may be spatially distributed either evenly or unevenly with respect to each other.

Figure 18:
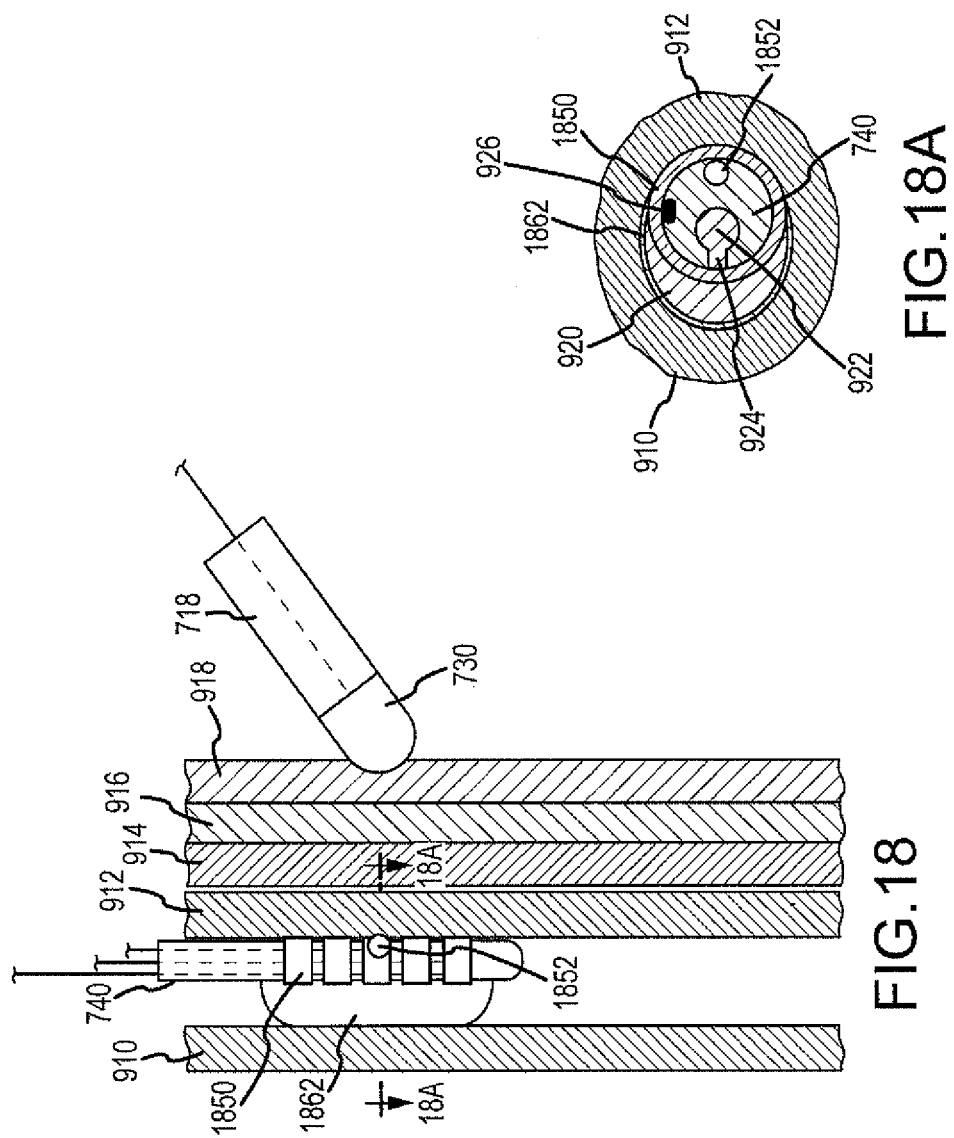
FIG. 18 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 18 and 18A show an exemplary embodiment of the monitoring, managing and/or protecting device and system 700 with distributed electrodes 1850 on the distal portion of the monitoring shaft 740. In such an embodiment, the monitoring electrodes are ring electrodes 1850. The embodiment also shows an inflatable/deflatable unidirectional balloon 1862 provided on one side of the distal portion of the monitoring shaft 740. Additionally, a thermal sensor 1852 is provided at the distal portion of the monitoring shaft 740. The thermal sensor 1852 is operatively connected to a modified electrical response assessment system/component (not shown) which is configured to measure the electrical and thermal characteristics of the tissue between the monitoring electrode 1850 and the ablation electrode 730, such as between the esophageal and endocardial electrodes.

Figure 19:
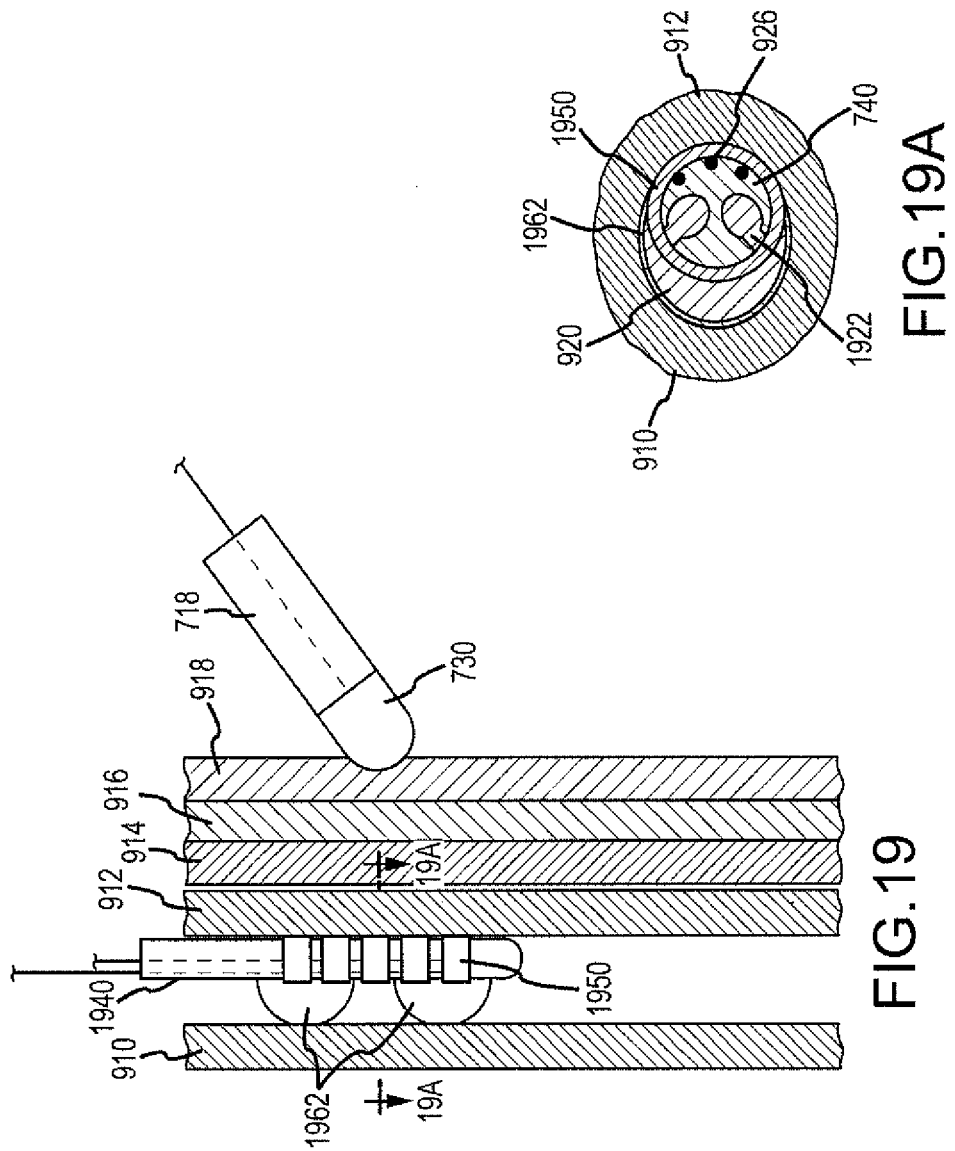
FIG. 19 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.
Figure 20:
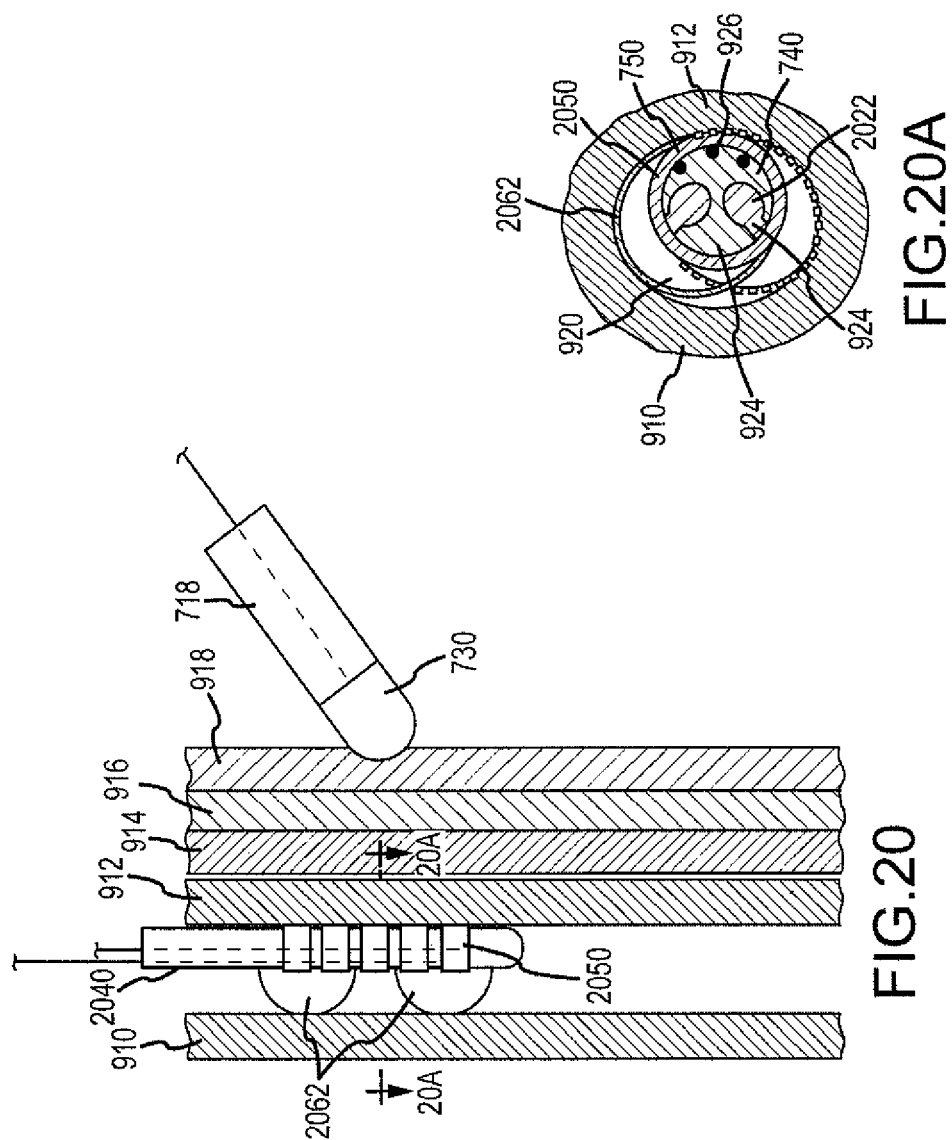
FIG. 20 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.
Figure 21:
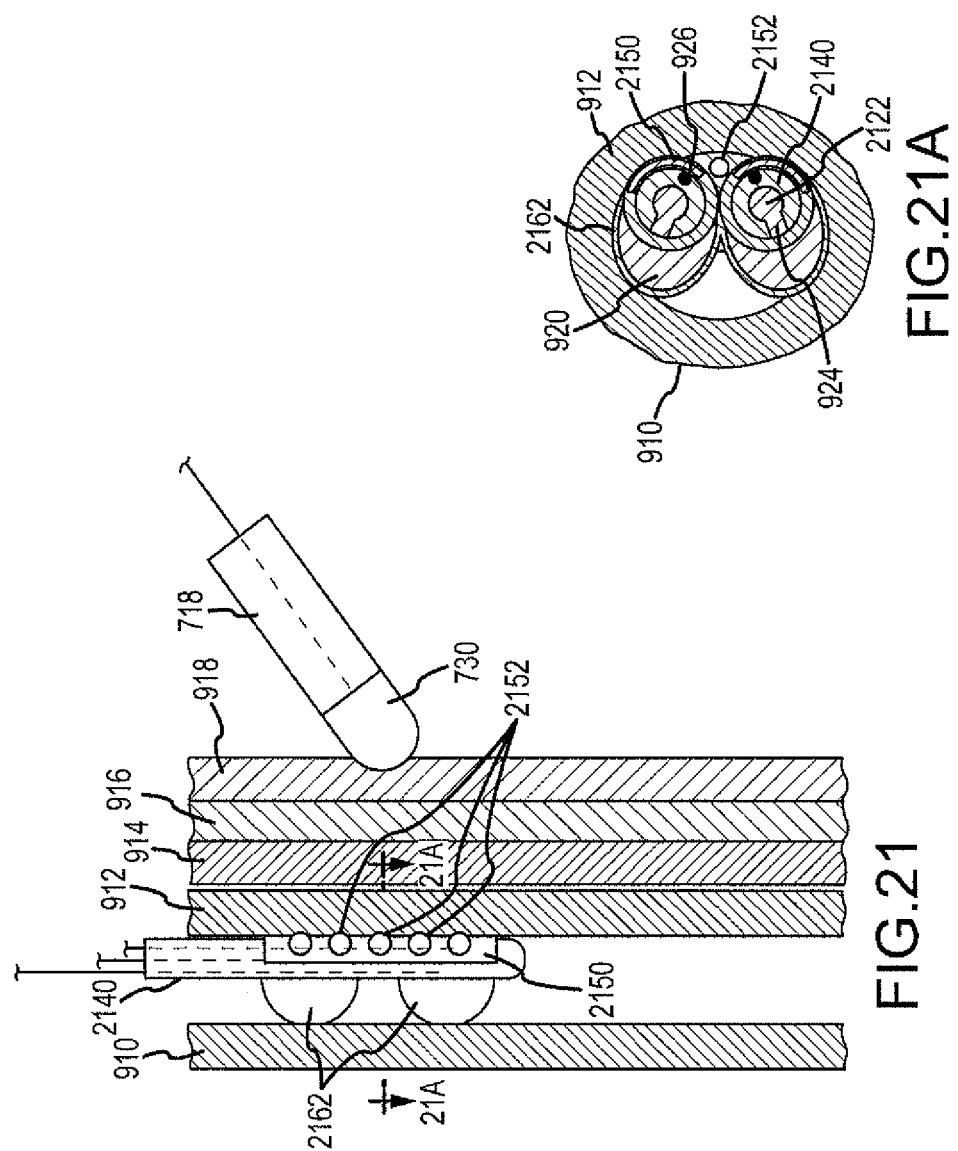
FIG. 21 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 19 through 21 show exemplary embodiments of the monitoring, managing and/or protecting device and system 700 with multiple balloons provided at the distal portion of the catheter shaft. FIGS. 19 and 19A show multiple longitudinally-aligned balloons 1962, FIGS. 20 and 20A show multiple obliquely-staggered balloons 2062, and FIGS. 21 and 21A show multiple obliquely-juxtaposed balloons 2162. FIGS. 19 and 20 also show the monitoring shaft 1940, 2040 having multiple fluid lumens 1922, 2022. The multiple obliquely positioned balloons 1962, 2062 allow coronal distention of the esophagus, thereby retracting the esophagus from the posterior wall of the atrium 918.

Figure 22:
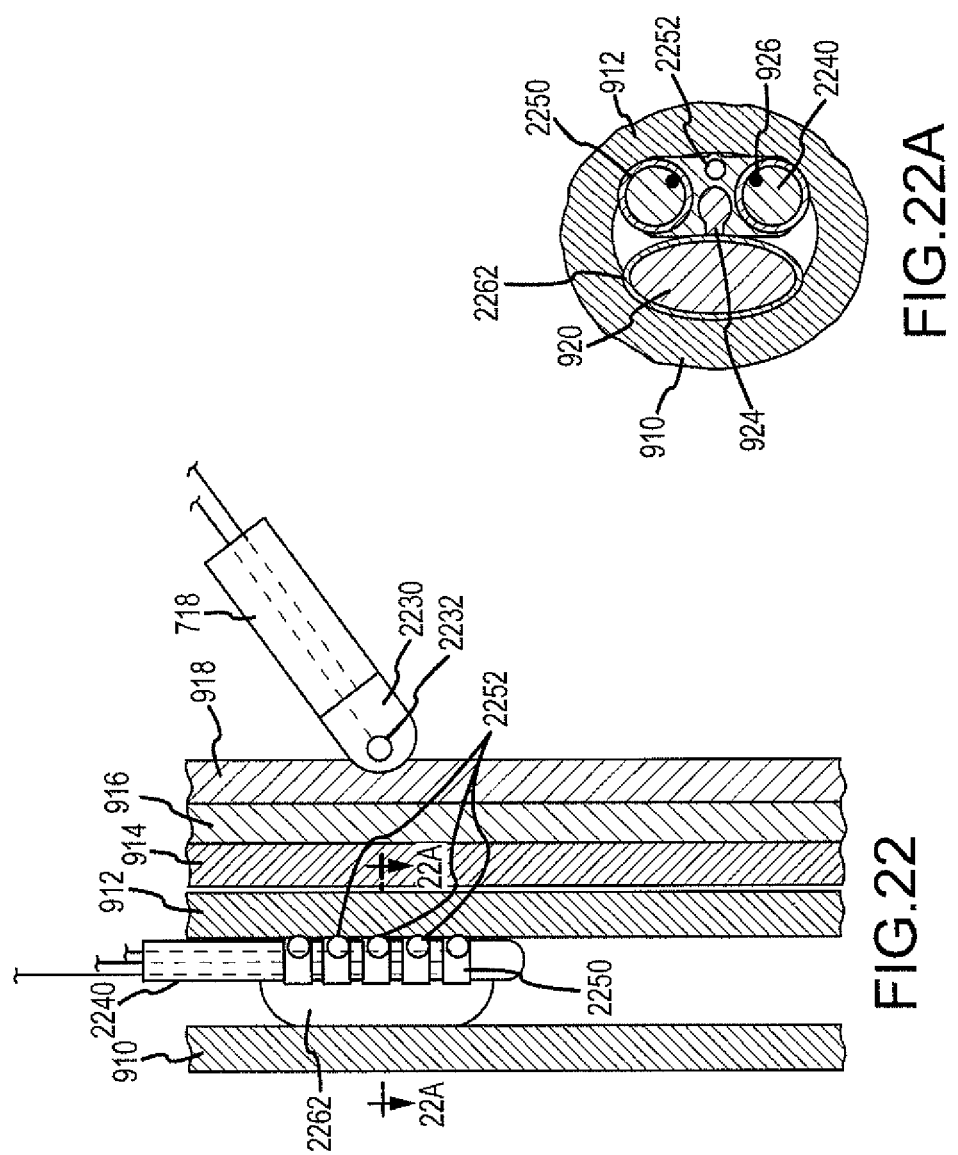
FIG. 22 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 21 through 22 show exemplary embodiments of the monitoring, managing and/or protecting device and system 700 with a dual monitoring shaft 2140, 2240. The distal portion of each monitoring shaft 2140, 2240 carries monitoring electrodes 2150, 2250 that may be electrically connected to each other (as a distributed uni-polar electrode) or electrically isolated from each other (as a bi-polar or multi-polar electrode). FIGS. 21 and 21A show the embodiment of a longitudinal electrode 2150 on a monitoring shaft 2140. FIG. 22 further shows an endocardial thermal sensor 2232 used in conjunction with the endocardial electrode 2230. FIGS. 21 through 22 also show the monitoring electrode 2150, 2250 provided with an array of thermal sensors 2152, 2252 which are operatively connected to a modified electrical response assessment system/component (not shown) which is configured to measure the electrical and thermal characteristics of the tissue between the monitoring electrode 2150, 2250 and the ablation electrode 730, 2230 such as between the esophageal and endocardial electrodes.

Figure 23:
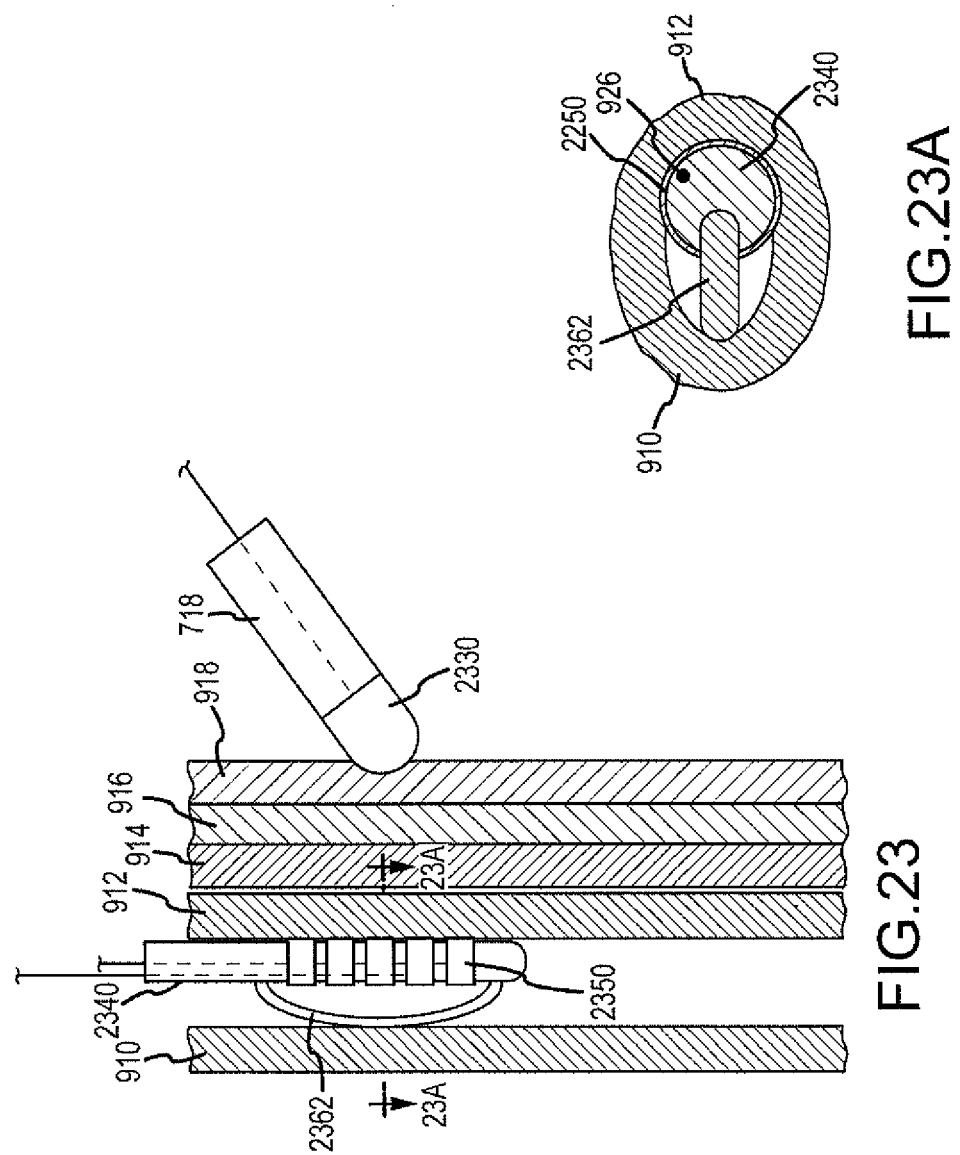
FIG. 23 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.
Figure 24:
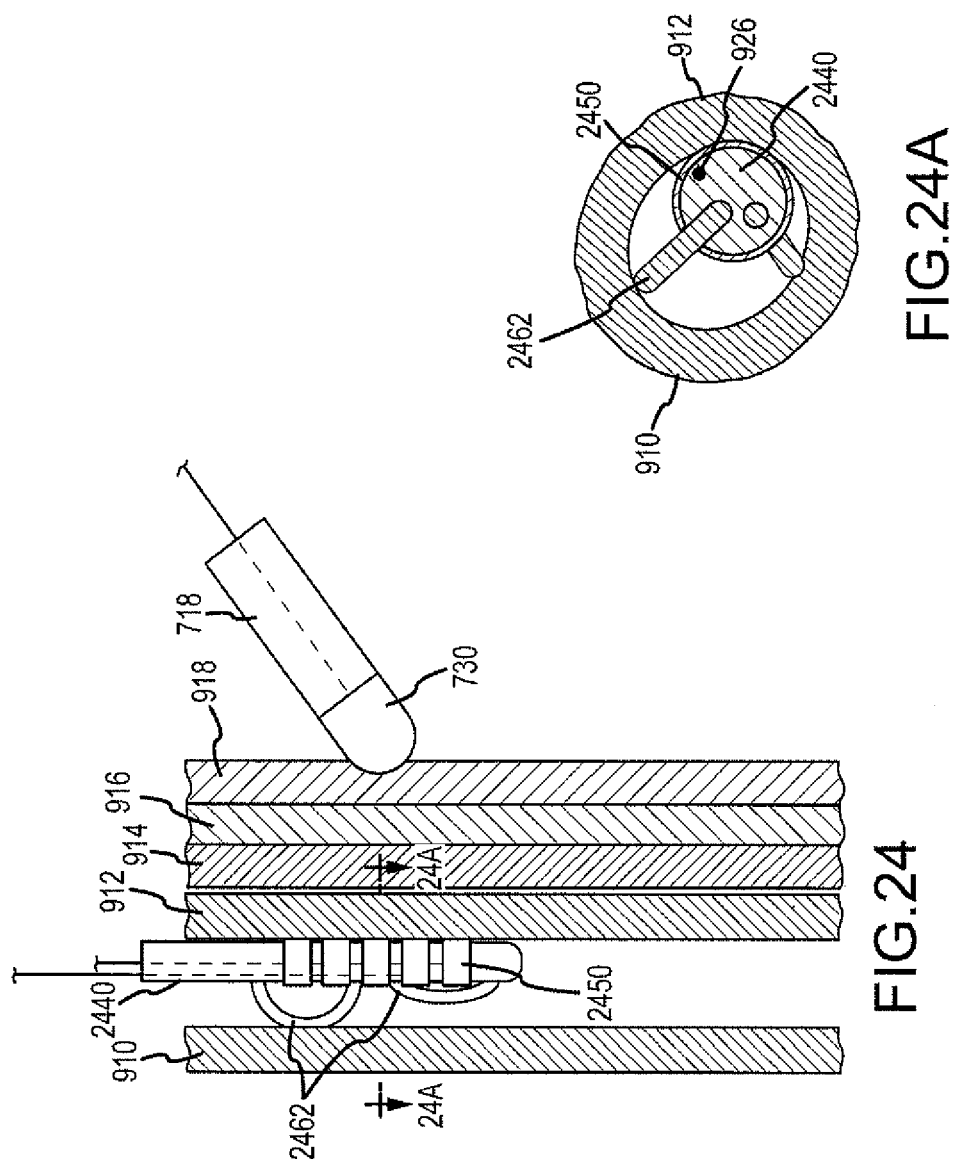
FIG. 24 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 23 through 24 show exemplary embodiments of the monitoring, managing and/or protecting device and system 700 with a deflectable anchoring device 2362, 2462 provided at the distal portion of the monitoring shaft 2340, 2440. In such embodiments, the deflectable anchoring device 2362, 2462 is shown as a single (see FIG. 23) and multiple (see FIG. 24) expandable/retractable semi-elliptic spring.

Figure 25:
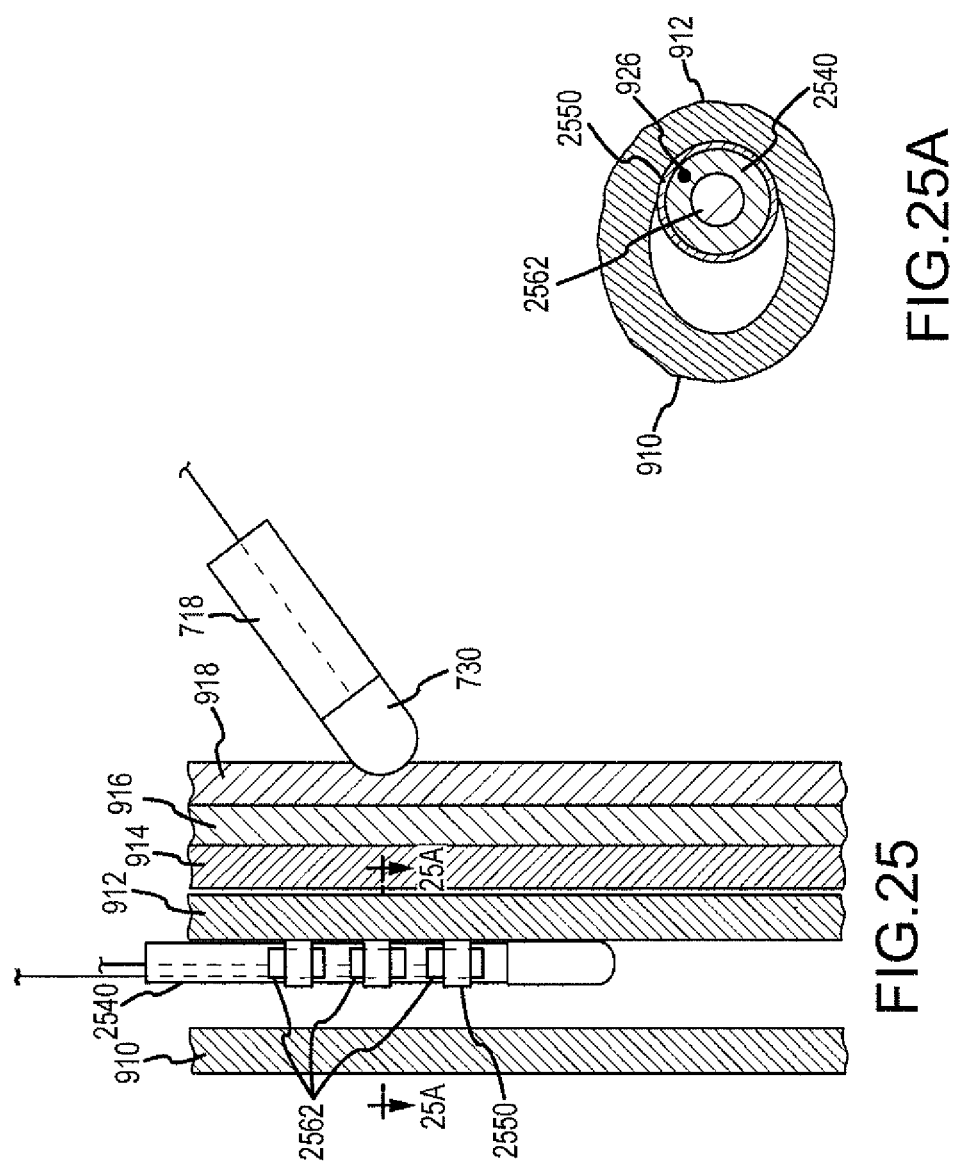
FIG. 25 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.
Figure 26:
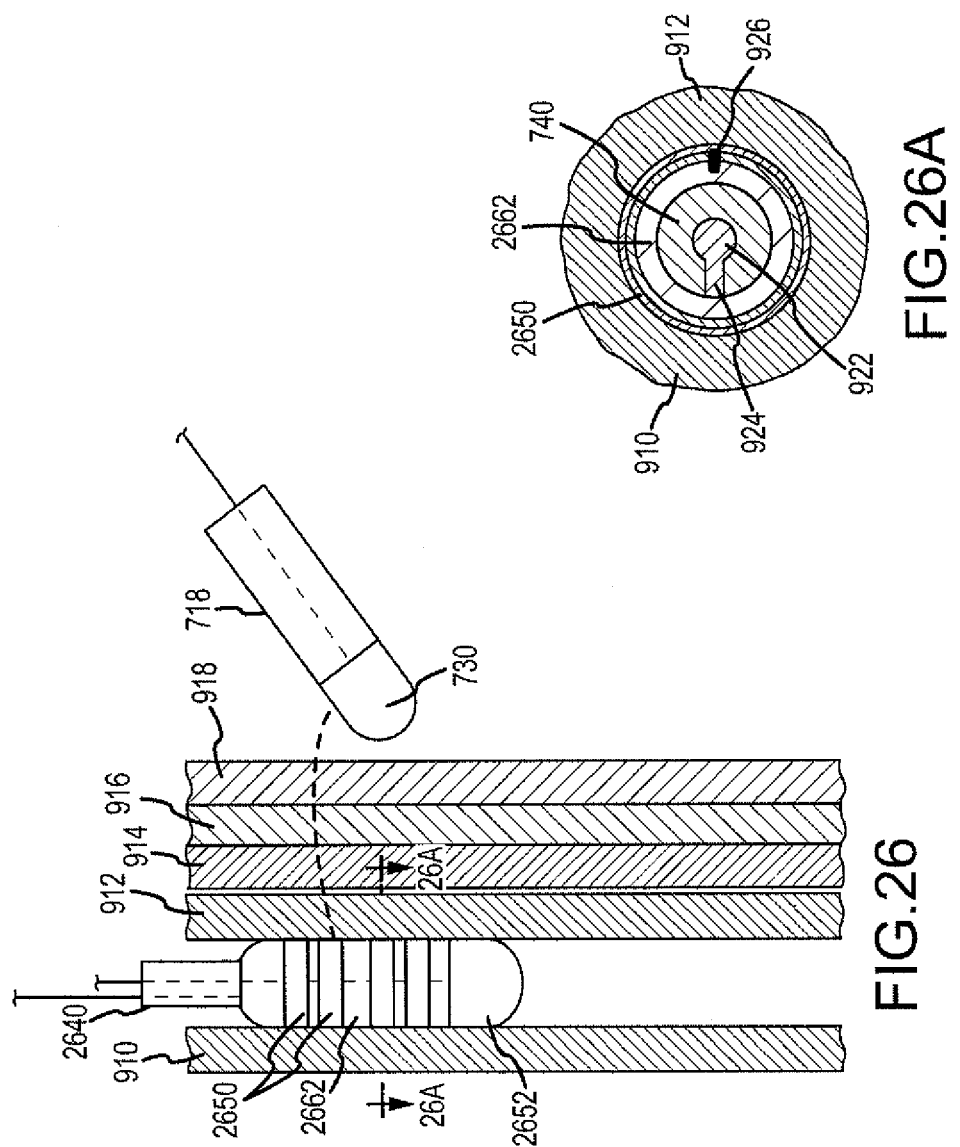
FIG. 26 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 25 through 26 show exemplary embodiments of the monitoring, managing and/or protecting device and system 700 with a magnetic-based anchoring device 2562, 2662. In FIGS. 25 and 25A, the magnetic material is provided at the distal portion of the monitoring shaft 2540. In FIGS. 26 and 26A, the magnetic material is provided as a magnetic fluid in the inflatable/deflatable balloon 2662 at the distal portion of the monitoring shaft 2640. The magnetic material helps positioning and anchoring the monitoring electrode 2650 by interacting with an external magnetic field.

FIGS. 27 through 35 show exemplary embodiments of different modes of configuring the monitoring, managing and/or protecting device and system 700.

Figure 27:
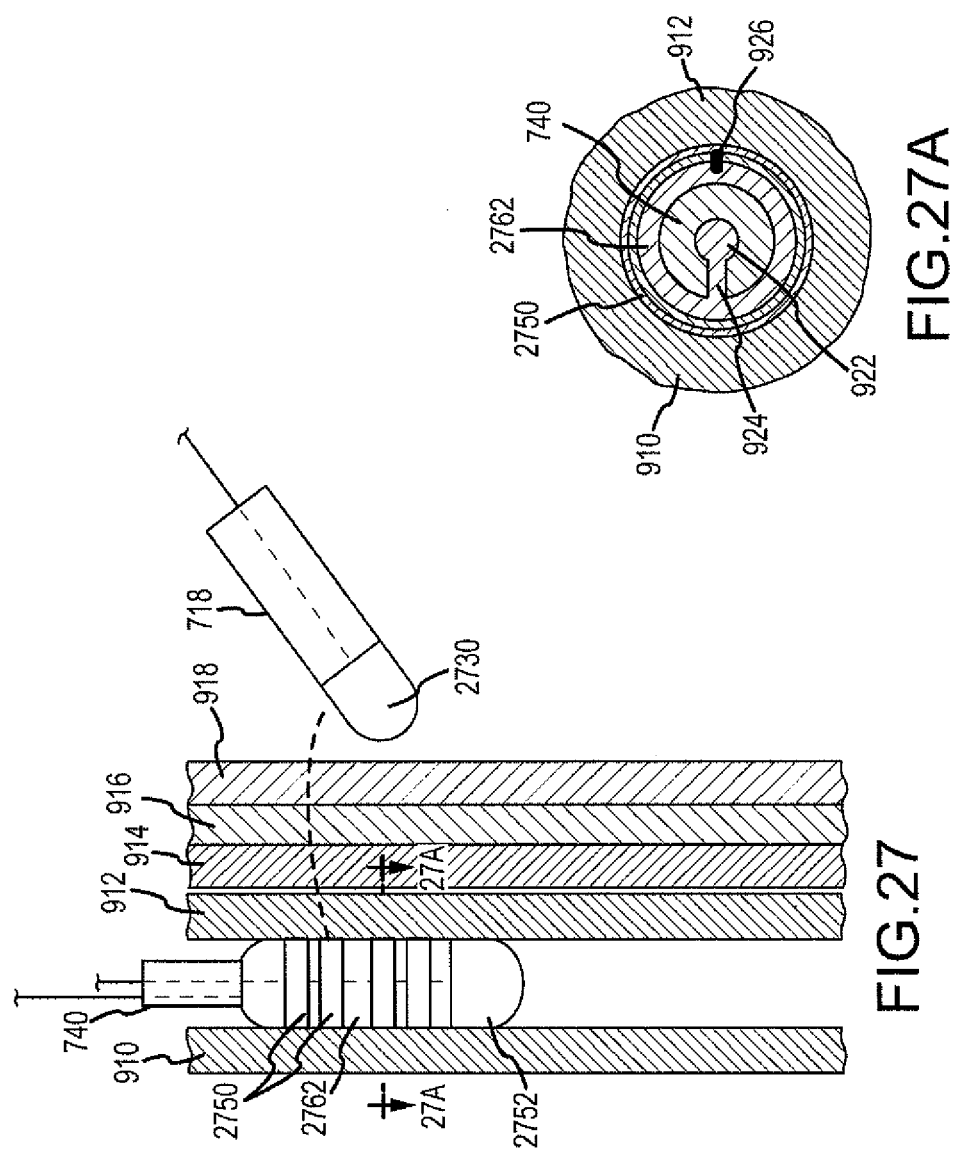
FIG. 27 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

In FIGS. 27 and 27A, the electrical response assessment system/component (not shown) is operatively connected to the electrode 2750 on the balloon 2762 and the electrode 2730 in the endocardial chamber and configured to monitor the proximity of the endocardial electrode 2730 to either the esophageal electrode 2750 or the endocardial wall 918. The dashed lines indicating an electric field.

Figure 28:
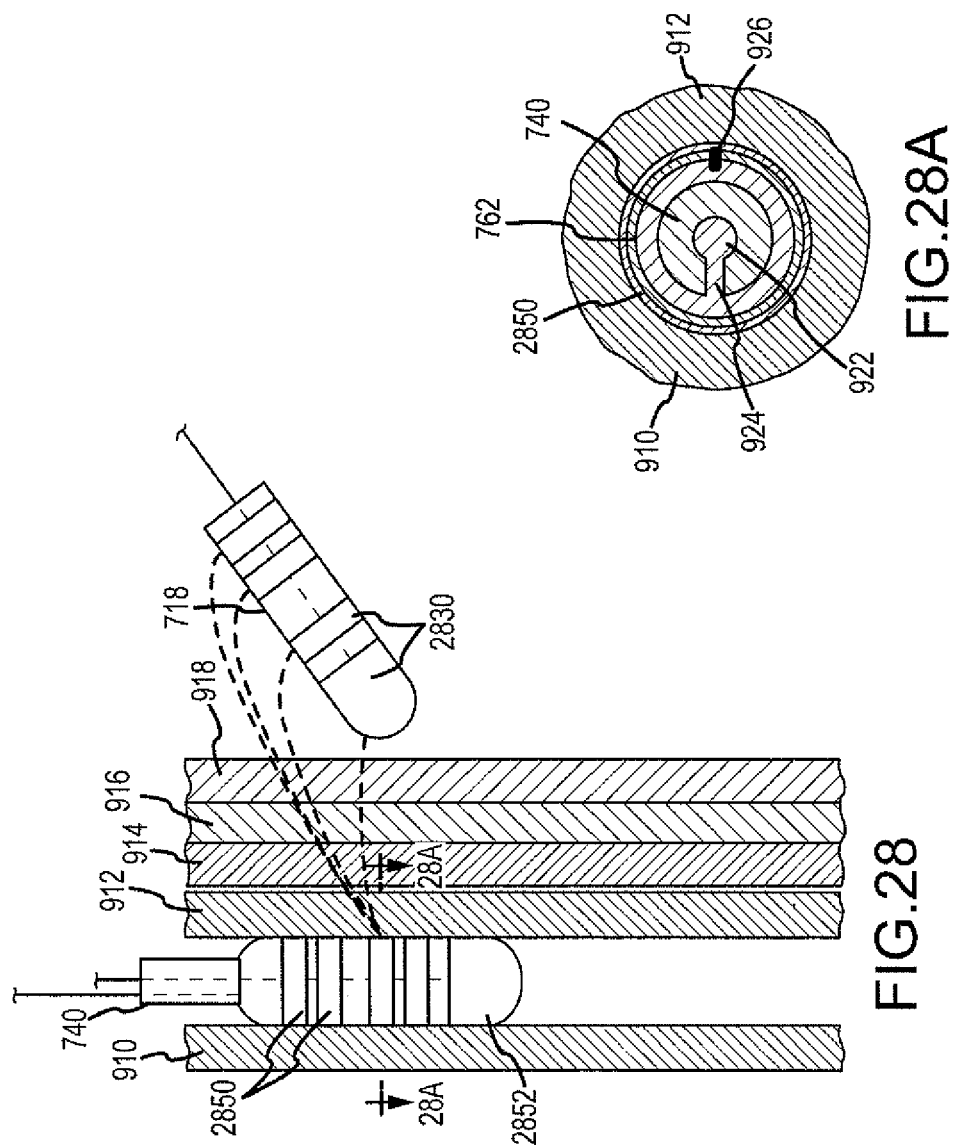
FIG. 28 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

In FIGS. 28 and 28A, an endocardial catheter 2830, such as an ablation catheter or a diagnostic catheter (e.g. a CS diagnostic catheter placed within the coronary vein via the coronary sinus), is configured as a reference electrode for calibrating the lumped electrical parameters of the tissue between the monitoring electrode 2850 and the endocardial electrodes 2830 when the endocardial electrode 2830 is not touching the endocardial wall 918.

Figure 29:
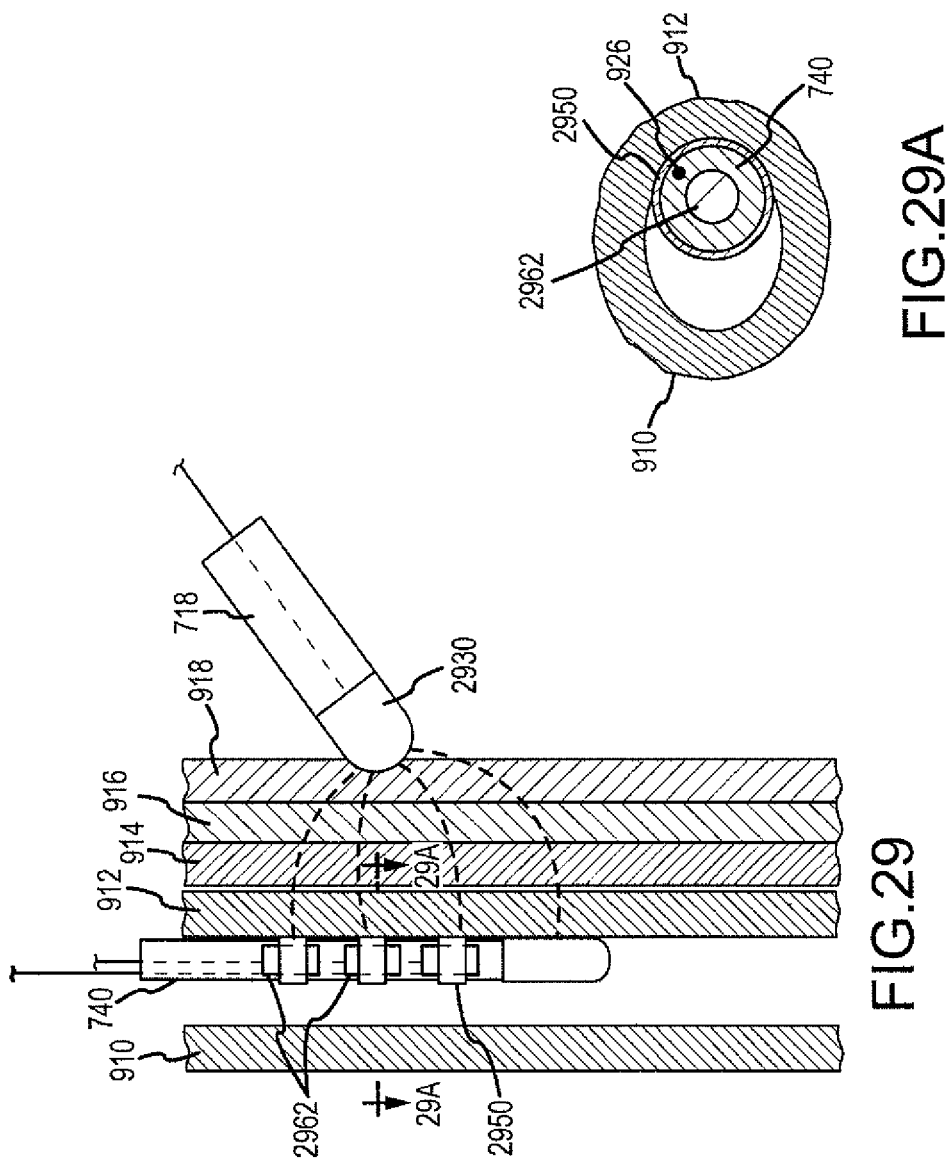
FIG. 29 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

In FIGS. 29 and 29A, the monitoring electrode 2950 is configured as a reference electrode for the endocardial electrode 2930 to monitor electrical parameters of tissue sensing, such as electrical coupling, before and during ablation of the posterior endocardial wall 918.

Figure 30:
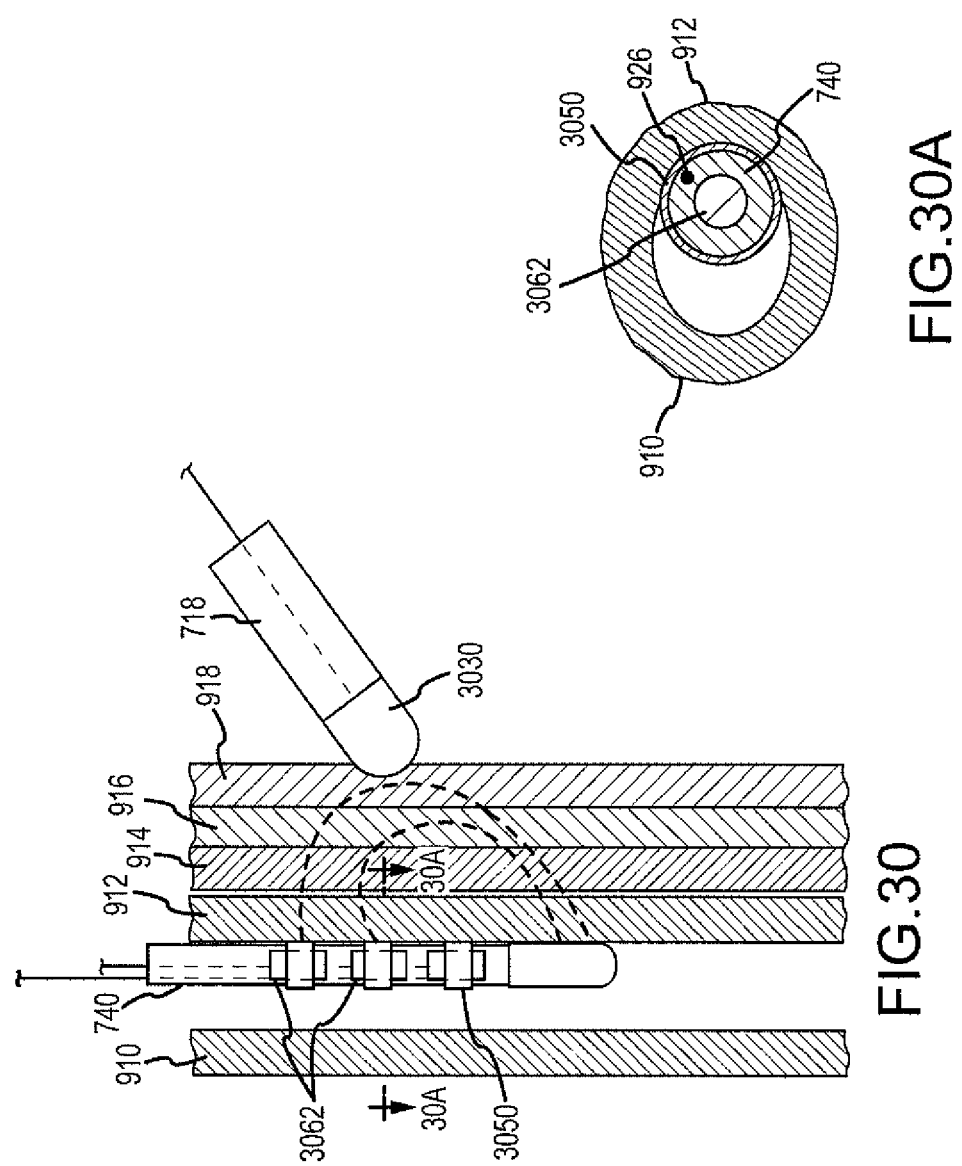
FIG. 30 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

In FIGS. 30 and 30A, the monitoring electrode 3050 is configured to monitor electrical parameters of tissue sensing in a bipolar or multi-polar mode.

Figure 31:
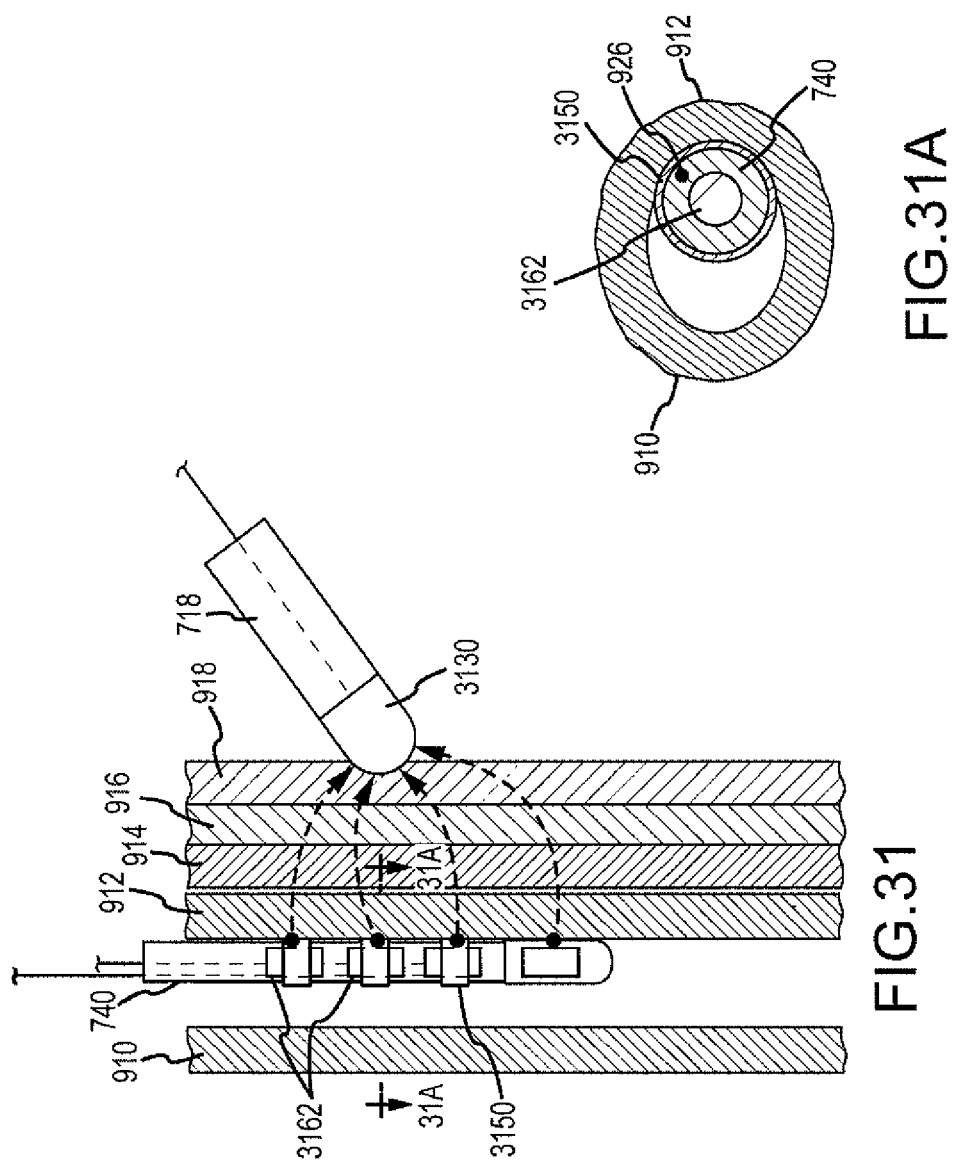
FIG. 31 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.
Figure 32:
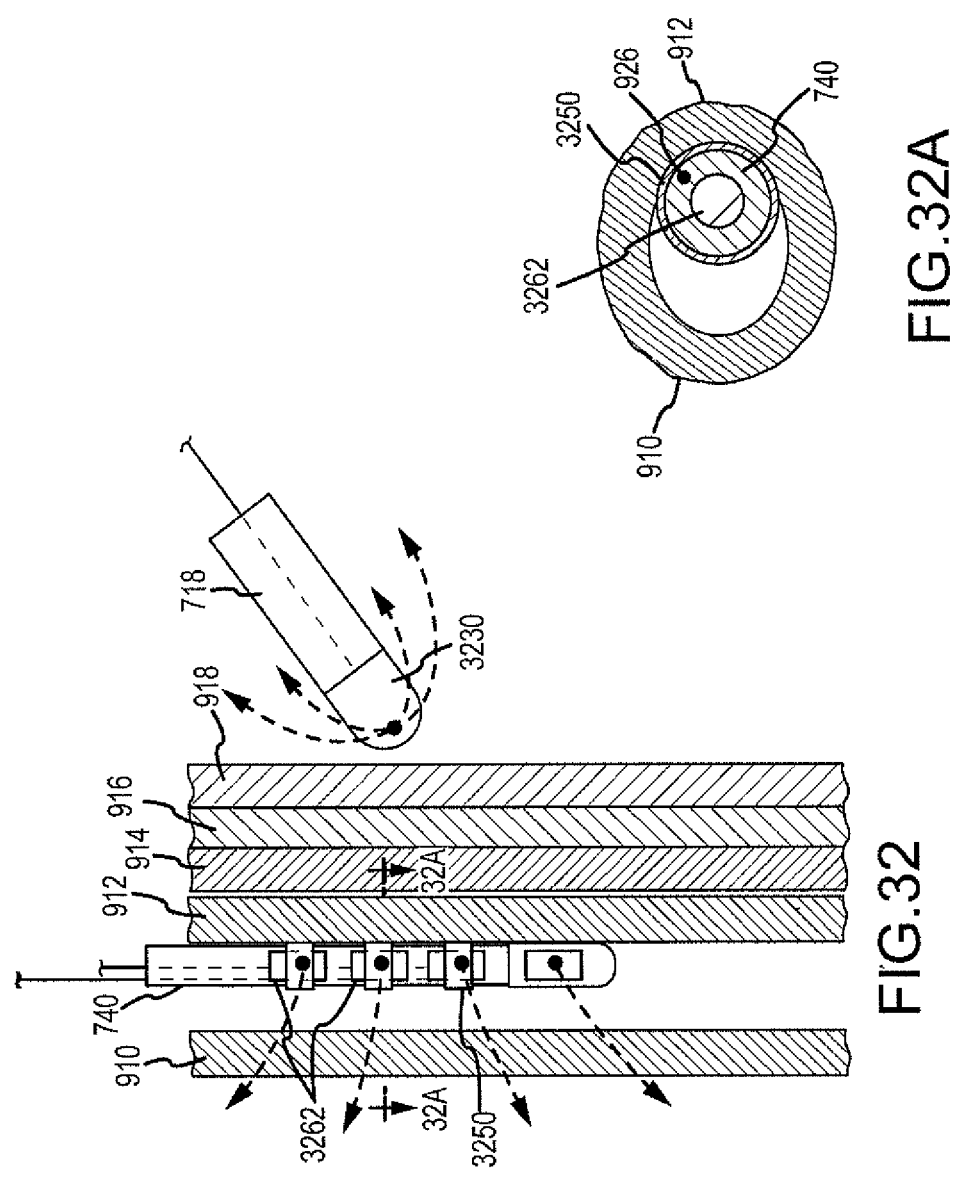
FIG. 32 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.
Figure 33:
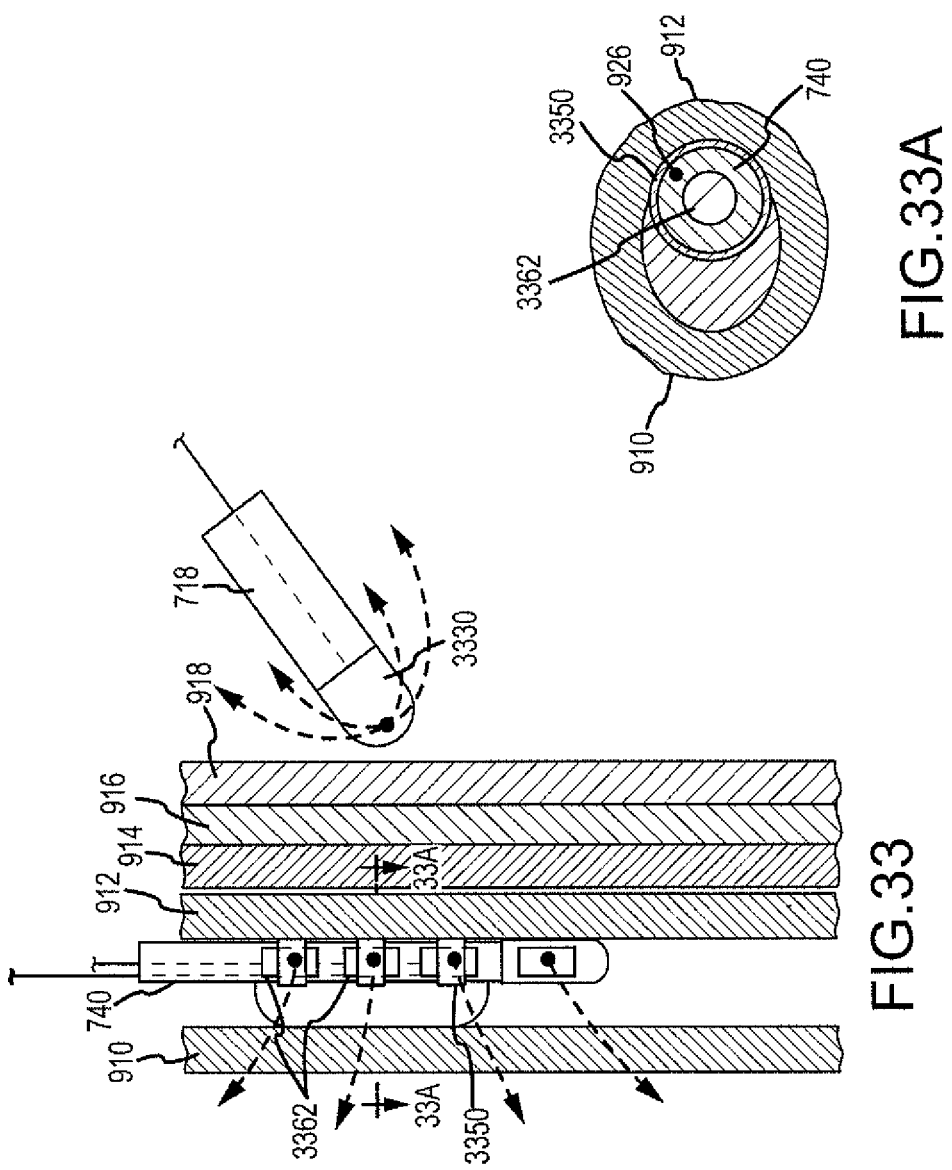
FIG. 33 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

In FIGS. 31 through 33, the dashed lines indicate the magnetic field. The monitoring electrode 3150, 3250, 3350 is configured to interact with the magnetic field of a magnetic endocardial electrode 3130, 3230, 3330. In FIGS. 31 and 31A the monitoring electrode 3150 is configured to attract, and/or be attracted to, the magnetic endocardial electrode 3130. In FIGS. 32 and 32A the monitoring electrode 3250 is configured to repel, and/or be repelled by, the magnetic endocardial electrode 3230. In FIGS. 33 and 33A the monitoring electrode 3350 is configured by means of a magnetic field controller interface (not shown) to be in a reactive mode (either attracting or repelling) with respect to magnetic endocardial electrode 3330 depending on the electrical parameters measured by the electrical response assessment system/component 760. For example, the monitoring and endocardial electrodes 3350, 3330 may be in an attracting mode at the beginning of ablation, and subsequently changed to be in a repelling mode upon reaching a threshold ablation stage.

Figure 34:
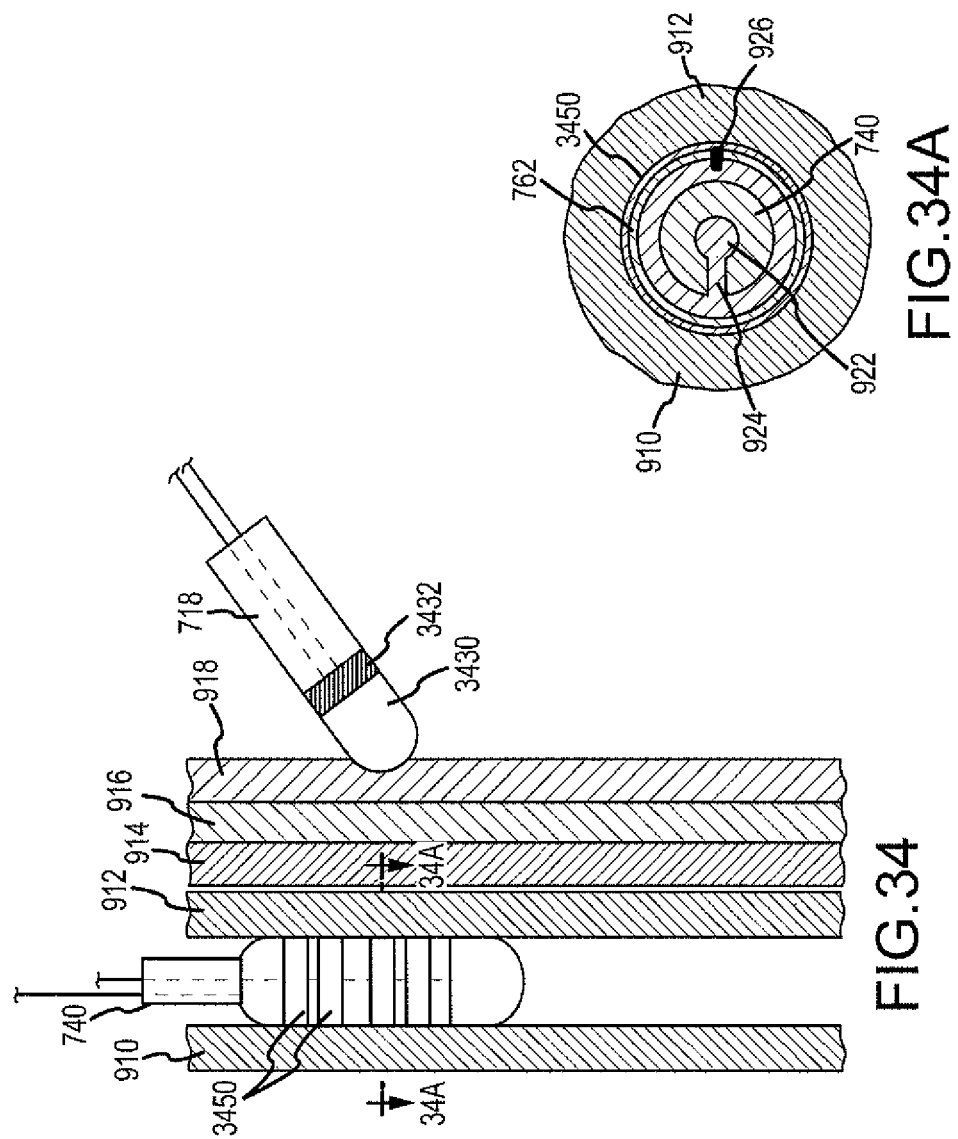
FIG. 34 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 34 and 34A show an exemplary embodiment of the monitoring, managing and/or protecting device and system 700 configured to interact with an endocardial ablation catheter 3430 that also has contact force sensor 3432. The contact force sensor 3432 is operatively connected to a modified electrical response assessment system/component (not shown) which is configured to measure the electrical characteristics of the tissue between the electrodes along with the contact force.

Figure 35:
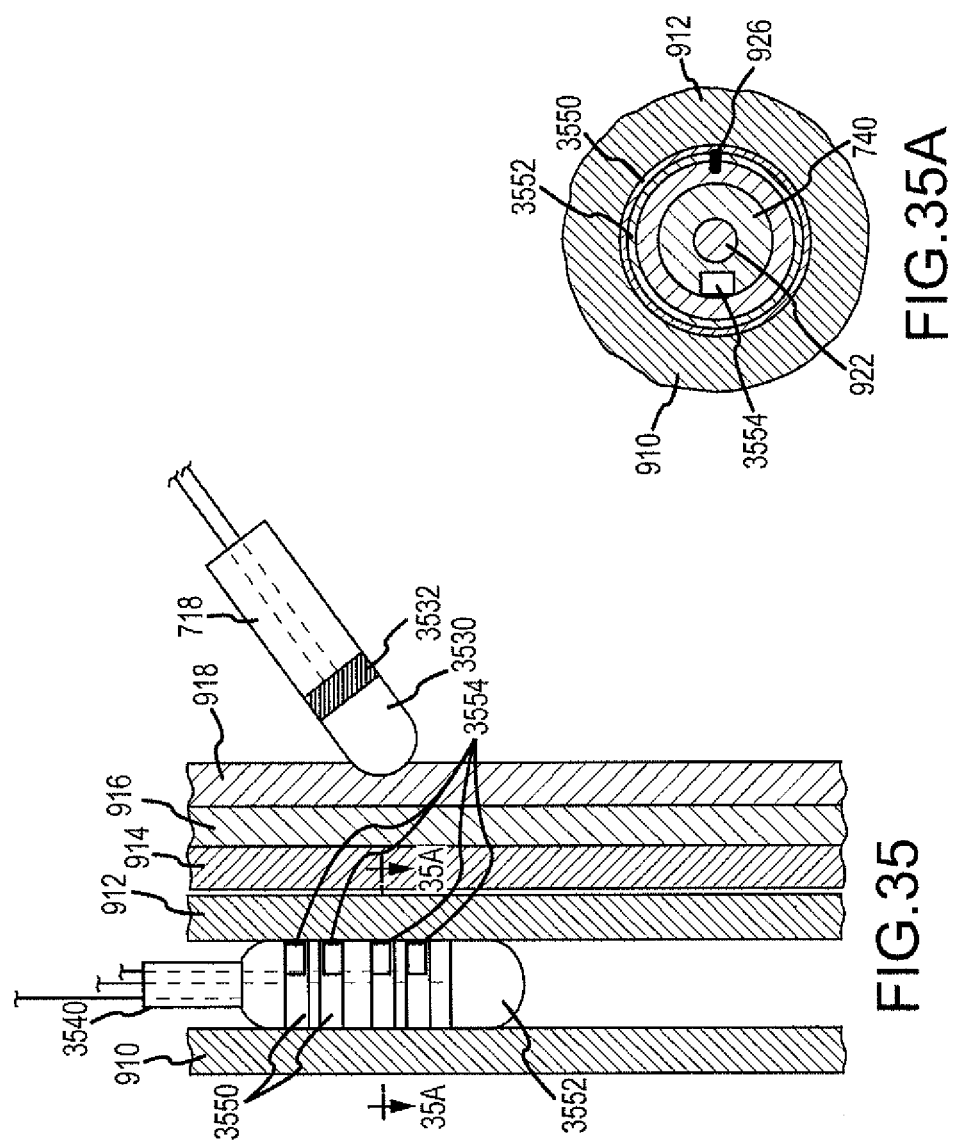
FIG. 35 is a partial cross-section diagrammatic view of an exemplary embodiment of a monitoring and protecting probe of a non-targeted tissue monitoring, managing and/or protecting system illustrated in FIGS. 7 and 8, wherein the probe is disposed within the esophagus of a patient during a medical procedure such as an ablation, in accordance with the present disclosure.

FIGS. 35 and 35A show an exemplary embodiment of the monitoring, managing and/or protecting device and system 700 provided with a position sensor 3554. The monitoring, managing and/or protecting device and system 700 along with the position sensor 3554 configured to interact with an endocardial electrode 3530 and provide the location of the endocardial electrode 3530 with respect to the monitoring electrode 3550. The position sensor 3554 is operatively connected to a modified electrical response assessment system/component (not shown) which is configured to measure the electrical characteristics of the tissue between the electrodes along with the relative position of the electrodes. As described herein, such position sensors include, but are not limited to, visual position sensors, encoders to measure a relative and/or an absolute position, magnetic position sensors, among others, and combinations thereof.

Figure 36:
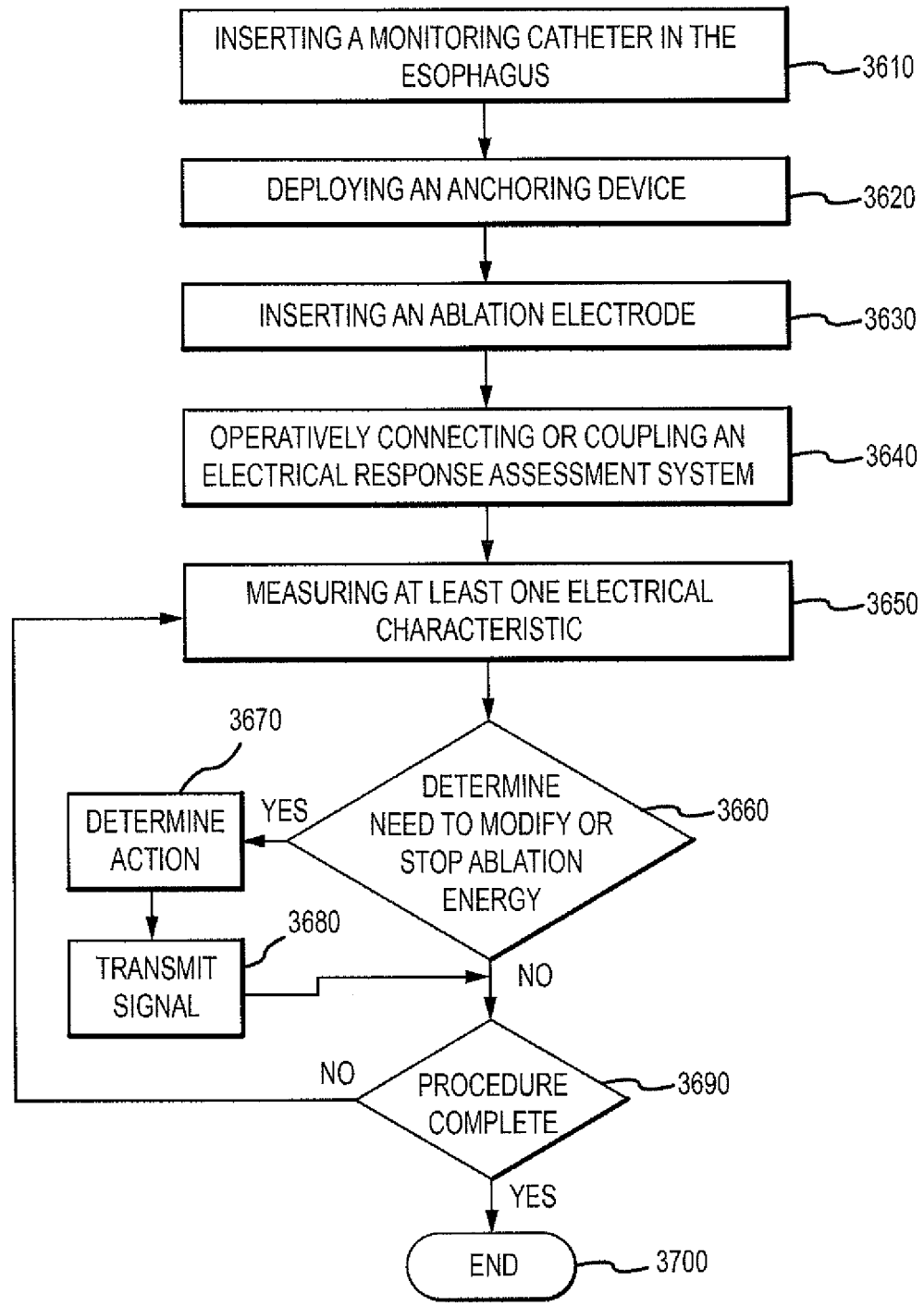
FIG. 36 is a flowchart showing an exemplary method of monitoring, managing and protecting non-targeted tissue during a medical procedure, such as an ablation, in accordance with the present disclosure.

FIG. 36 is a flow chart showing an exemplary method of monitoring, managing and/or protecting non-targeted tissue during a medical procedure as described herein. The exemplary method comprises the following steps:

Inserting a monitoring catheter in the patient's esophagus 3610 such that an electrode on the monitoring catheter is aligned or positioned with and facing the posterior wall of the atrium;

Deploying an anchoring device 3620 such that the anterior surface of the anchoring device is facing the posterior wall of the atrium. As described herein, such anchoring devices include, but are not limited to, various types of inflatable and deflatable balloons, fluid based structures, deflectable wire-based structure, such as an expandable/retractable spring (e.g. a coil spring, semi-elliptic spring, cantilever spring), a mesh, or a stent, or a magnetic-based structure, such as a coil (i.e. an electromagnetic coil), ferromagnet, permanent magnet, or electromagnet.

Inserting an ablation electrode 3630 into the endocardial chamber;

Operatively connecting or coupling an electrical response assessment system and/or component 3640 to the electrode on the monitoring catheter and to the electrode in the endocardial chamber;

Measuring at least one electrical characteristic 3650 of the tissue proximate the monitoring electrode or the tissue between the monitoring electrode and the ablation electrode;

Determining, during the ablation procedure, from the electrical characteristics 3660 measured by the electrical response assessment system and/or component whether it is necessary to modify or stop the ablation energy delivered to the endocardial electrode to prevent or minimize damage to the non-targeted tissue;

If the need to modify or stop the ablation energy exists, determining the necessary modification or notifying the practitioner of the potential damage 3670, and transmitting the corresponding signal 3680;

Once the signal is transmitted (or if there was no need for the signal), determine if the procedure is complete 3690, and if so, end 3700, otherwise return to measure additional electrical characteristics in step 3650 until complete 3700.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

The invention claimed is:

1. A monitoring, managing and protecting system for providing protection to non-targeted tissue during an ablation of the posterior wall of the atrium, the monitoring system comprising:
    a) a monitoring probe comprising a tubular body and a monitoring shaft, wherein said monitoring shaft has a proximal portion, a distal portion, an anterior surface, and a posterior surface;
    b) an anchoring device provided at the distal portion of the monitoring shaft, wherein the anchoring device is configured to anchor the monitoring shaft within an esophagus, wherein the anchoring device comprises at least one of a fluid based structure, a deflectable wire-based structure, and a magnetic-based structure;
    c) at least one monitoring electrode, said at least one monitoring electrode configured to be located proximate said non-targeted tissue, wherein the at least one monitoring electrode is configured to acquire an electrical signal from the non-targeted tissue; and
    d) an electrical response assessment system, wherein said electrical response assessment system is operatively connected to said at least one monitoring electrode, and said electrical response assessment system is configured to (i) calculate a product of power applied during a duration of the ablation, wherein the product comprises a total energy applied during the duration; (ii) measure a complex impedance according to said electrical signal, said complex impedance having at least a resistance and a reactance or an impedance magnitude and a phase angle, and (iii) determine whether said non-targeted tissue will be damaged before damage occurs based on said calculation of said product of power applied over said duration of the ablation and at least one of said resistance, said reactance, said impedance magnitude, or said phase angle, wherein the electrical response assessment system further determines whether said non-targeted tissue will be damaged before damage occurs by predicting the temperature of a tissue at a predetermined depth below a surface of the non-targeted tissue.

2. The monitoring system in claim 1, wherein the fluid based structure is an inflatable/deflatable balloon.

3. The monitoring system in claim 2, wherein the inflatable/deflatable balloon comprises a plurality of segments.

4. The monitoring system in claim 3, wherein each segment of the inflatable/deflatable balloon contains a different fluid.

5. The monitoring system in claim 1, wherein the deflectable wire-based structure comprises at least one of an expandable/retractable spring, an expandable/retractable mesh, and an expandable/retractable stent.

6. The monitoring system in claim 5, wherein the expandable/retractable spring comprises at least one of a coil spring, a semi-elliptic spring, and a cantilever spring.

7. The monitoring system in claim 1, wherein the magnetic-based structure comprises at least one of a coil, a ferromagnet, a permanent magnet, and an electromagnet.

8. The monitoring system in claim 1, wherein the at least one monitoring electrode is located on said anterior surface of the distal portion of the monitoring shaft.

9. The monitoring system in claim 1, wherein the at least one monitoring electrode is on an anterior surface of the distal portion of the anchoring device that is separate from said anterior surface of said monitoring shaft.

10. The monitoring system in claim 1, wherein the at least one monitoring electrode is a metal electrode, said metal electrode comprising a metalized film.

11. The monitoring system in claim 1, wherein the at least one monitoring electrode is a conductive polymer electrode.

12. The monitoring system in claim 1, wherein the at least one monitoring electrode is selected from the group consisting of a ring electrode, a spot electrode, a spiral electrode, an array electrode, a mesh electrode, and a longitudinal electrode.

13. The monitoring system in claim 12, wherein the at least one monitoring electrode comprises multiple electrodes disposed in a plane perpendicular to a longitudinal axis of said monitoring probe.

14. The monitoring system in claim 13, wherein one of the multiple electrodes comprises ring electrodes.

15. The monitoring system in claim 1, further comprising a thermal sensor, wherein said thermal sensor is operatively connected to the electrical response assessment system and said monitoring system is configured to measure the electrical and thermal characteristics of tissue between an anterior wall of the esophagus and a posterior endocardial wall of the atrium.

16. A catheter system for providing esophageal protection during ablation, the catheter system comprising:
    a) an esophageal catheter comprising a tubular body having a catheter shaft, wherein the catheter shaft has a proximal portion and a distal portion;

b) an anchoring means provided at the distal portion of the catheter shaft, wherein the anchoring means has an anterior surface and a posterior surface;
c) at least one electrode on the anterior surface of the anchoring means;
d) at least one other electrode configured to be located proximate an atrium; and
e) an electrical response assessment system operatively connected to the at least one electrode on the anchoring means and the at least one other electrode proximate the atrium, said electrical response assessment system configured to: (i) calculate a product of power applied during the duration of the ablation, wherein the product comprises a total energy applied during the duration; (ii) measure a complex impedance of a tissue between the at least one electrode on the anchoring means and the at least one other electrode configured to be located proximate the atrium, the complex impedance including at least a reactance and a resistance or an impedance magnitude and a phase angle; (iii) calculate a metric according to said calculation of said product of power applied during the duration of the ablation and at least one of said reactance, said resistance, said impedance magnitude, or said phase angle of said complex impedance by applying a mathematical algorithm that accepts as input at least said calculation of said product of power applied during the duration of the ablation and said at least one of said reactance, said resistance, said impedance magnitude, or said phase angle of said complex impedance and outputs said metric; and (iv) determine if the tissue between the at least one electrode on the anchoring means and the at least one other electrode configured to be located proximate the atrium is being damaged before damage occurs in an ablation procedure according to said metric, wherein the electrical response assessment system further determines whether the tissue between the at least one electrode on the anchoring means will be damaged before damage occurs by predicting the temperature at a predetermined depth below a surface of the tissue.

17. The catheter system for providing esophageal protection during ablation in claim 16, further comprising a robotic control and guidance system, said robotic control and guidance system configured to control a position of said at least one other electrode, and comprising an electronic control system, said electronic control system operatively connected to said electrical response assessment system, such that said electrical response assessment system is capable of controlling said at least one other electrode based on the measure of the electrical characteristics of the tissue between the at least one electrode on the anchoring means and the at least one other electrode configured to be located proximate the atrium.

18. The catheter system for providing esophageal protection during ablation in claim 16, wherein said electrical response assessment system is further configured to receive an ablation temperature and to calculate said metric further according to said ablation temperature.

19. A monitoring, managing and protecting system for providing protection to non-targeted tissue during an ablation of the posterior wall of the atrium, the monitoring system comprising:
a) a monitoring probe comprising a tubular body and a monitoring shaft, wherein said monitoring shaft has a proximal portion, a distal portion, an anterior surface, and a posterior surface;
b) an anchoring device provided at the distal portion of the monitoring shaft, wherein the anchoring device comprises at least one of a fluid based structure, a deflectable wire-based structure, and a magnetic-based structure;
c) at least one monitoring electrode, said at least one monitoring electrode configured to be located proximate said non-targeted tissue, wherein the at least one monitoring electrode is configured to acquire an electrical signal from the non-targeted tissue; and
d) an electrical response assessment system, wherein said electrical response assessment system is operatively connected to said monitoring electrode, and said electrical response assessment system is configured to (i) calculate a product of power applied during a duration of the ablation, wherein the product comprises a total energy applied during the duration; (ii) measure a complex impedance according to said electrical signal, said complex impedance having at least a resistance, a reactance, an impedance magnitude, and a phase angle, and (iii) determine whether said non-targeted tissue will be damaged before damage occurs based on said calculation of said product of power applied during the duration of the ablation, said resistance, said reactance, said impedance magnitude, and said phase angle, wherein the electrical response assessment system further determines whether said non-target tissue will be damaged before the damage occurs by predicting the temperature of a tissue at a predetermined depth below a surface of the non-targeted tissue.

20. The monitoring system in claim 19, wherein said electrical response assessment system is further configured to receive an ablation temperature and to calculate said metric further according to said ablation temperature.

* * * * *